(12) United States Patent
Schall et al.

(10) Patent No.: US 6,699,677 B1
(45) Date of Patent: Mar. 2, 2004

(54) TETHERED LIGANDS AND METHODS OF USE

(75) Inventors: Thomas J. Schall, Menlo Park, CA (US); Brett Premack, San Francisco, CA (US); Zhenhua Miao, San Jose, CA (US); Zheng Wei, Redwood City, CA (US)

(73) Assignee: ChemoCentryx, Inc., San Carlos, CA (US)

( * ) Notice: Subject to any disclaimer, the term of this patent is extended or adjusted under 35 U.S.C. 154(b) by 267 days.

(21) Appl. No.: 09/721,908

(22) Filed: Nov. 24, 2000

Related U.S. Application Data

(60) Provisional application No. 60/186,626, filed on Mar. 3, 2000, and provisional application No. 60/172,979, filed on Dec. 20, 1999.

(51) Int. Cl.[7] .................. G01N 33/567; G01N 33/566; C12P 21/04; C12N 5/00
(52) U.S. Cl. .................. 435/7.24; 435/69.7; 435/325; 436/501
(58) Field of Search .................. 436/501; 435/7.24, 435/69.7, 325

(56) References Cited

U.S. PATENT DOCUMENTS 5,817,527 A  10/1998  Piran et al. .................. 436/527

5,854,005 A  12/1998  Coller

FOREIGN PATENT DOCUMENTS

| EP | 0 626 450 A2 | 11/1994 |
|----|----|----|
| WO | WO 94/19694 A1 | 9/1994 |
| WO | WO 97/17375 A1 | 5/1997 |
| WO | WO 97/27299 A1 | 7/1997 |
| WO | WO 98/49557 A1 | 11/1998 |

OTHER PUBLICATIONS

Csanaky, G., et al.; Adhesion receptors on peripheral blood leukemic B cells. A comparative study on B cell chronic lymphocytic leukemia and related lymphoma/leukemias; *Leukemia;* 1997; pp. 408–415; vol. 11.

(List continued on next page.)

*Primary Examiner*—Hankyel T. Park
(74) *Attorney, Agent, or Firm*—Townsend and Townsend and Crew LLP

(57) ABSTRACT

The invention provides methods, reagents and devices for analysis of receptor ligand interactions, determining the profile of receptor expression in cells and cell populations, and diagnostic and drug screening methods. The invention makes use of immobilized tethered ligand fusion proteins having a ligand domain, a stalk domain, and optionally an immobilization domain.

37 Claims, 6 Drawing Sheets

OTHER PUBLICATIONS

Almenoff, June S., et al.; Induction of Heat–stable Enterotixin Receptor Activity by a Human Alu Repeat; *The Journal of Biological Chemistry;* Jun. 17, 1994; pp. 16610–16617; vol. 269. No. 24.

Almenoff, June S. et al.; Ligand–based histochemical localization and capture of cells expressing heat–stable enterotoxin receptors; *Molecular Microbiology;* 1993; pp. 865–873; vol. 8, No. 5.

Baba, Masataka, et al.; Identification of CCR6, the Specific Receptor for a Novel Lymphocyte–directed CC Chemokine LARC; *The Journal of Biological Chemistry;* Jun. 6, 1997; pp. 14893–14898; vol. 272, No. 23.

Bazan, J. Fernando, et al.; Fractalkine: a new class of membrane–bound chemokine with a $CX_3C$ motif; *Nature;* Feb. 13, 1997; pp. 640–644; vol. 385.

Bleul, Conrad C., et al.; The lymphocyte chemoattractant SDF–1 is a ligand for LESTR/fusion and blocks HIV–1 entry; *Nature;* Aug. 29, 1996; pp. 829–833; vol. 382.

Chan, Po–Ling, et al.; VLA–4 Integrin Mediates Lymphocyte Migration on the Inducible Endothelial Cell Ligand VCAM–1 and the Extracellular Matrix Ligand Fibronectin; *The Journal of Biological Chemistry;* Nov. 25, 1993; pp. 24655–24664; vol. 268, No. 33.

Chen, JI, et al.; Tethered Ligand Library for Discovery of Peptide Agonists; *The Journal of Biological Chemistry;* Oct. 6, 1995; pp. 23398–23401; vol. 270, No. 40.

Combadiere, Christophe, et al.; Identification of $CX_3CR1$: A chemotactic receptor for the human $CX_3C$ chemokine fractalkine and a fusion coreceptor for HIV–1; *The Journal of Biological Chemistry;* Sep. 11, 1998; pp. 23799–23804; vol. 273, No. 37.

Davis, Samuel, et al.; The Receptor for Ciliary Neurotrophic Factor; *Science;* Jul. 5, 1991; pp. 59–63, vol. 253.

Doorbar, John, et al.; Isolation of a Peptide Antagonist to the Thrombin Receptor using Phage Display; *J. Mol. Biol;* 1994; pp. 361–369; vol. 244.

Farber, J.M.; Chemokines. lymphocytes, and HIV; *Brazilian Journal of Medical and Biological Research;* 1998; pp. 11–17; vol. 31, No. 1.

Fong, Alan M.; et al.; Fractalkine and $CX_3CR1$ Mediate a Novel Mechanism of Leukocyte Capture, Firm Adhesion, and Activation under Physiologic Flow; *J. Exp. Med.;* Oct. 19, 1998; pp. 1413–1419; vol. 188; No. 8.

Fong, Alan M., et al; Ultrastructure and Function of the Fractalkine Mucin Domain in $CX_3C$ Chemokine Domain Presentation; *The Journal of Biological Chemistry;* Feb. 11, 2000; pp. 3781–3786; vol. 275, No. 6.

Gao, Ji–Liang, et al.; Identification of a Mouse Eosinophil Receptor for the CC Chemokine Eotaxin; *Biochemical and Biophysical Research Communications;* 1996; pp. 679–684; vol. 223.

Gosling, Jennifa, et al.; Cutting Edge: Identification of a Novel Chemokine Receptor That Binds Dendritic Cell–and T Cell–Active Chemokines Including ELC, SLC, and TECK; *The Journal of Immunology;* 2000; pp. 2851–2856.

Haskell, Christopher A., et al.; Molecular Uncoupling of Fractalkine–mediated Cell Adhesion and Signal Transduction; *The Journal of Biological Chemistry;* Apr. 9, 1999; pp. 10053–10058; vol. 274, No. 15.

Hennecke, Meike, et al.; A selection system to study C5a–C5a–receptor interactions; Phage display of a novel C5a anaphylatoxin, Fos–C5A$^{Ala27}$; *Gene;* 1997; pp. 263–272; vol. 184.

Horuk, Richard, et al.; The CC Chemokine I–309 Inhibits CCR8–dependent Infection by Diverse HIV–1 Strains; *The Journal of Biological Chemistry;* Jan. 2, 1998; pp. 386–391; vol. 273, No. 1.

Imai, Toshio, et al.; Identification and Molecular Characterization of Fractalkine Receptor $CX_3CR1$, which Mediates Both Leukocyte Migration and Adhesion; *Cell;* Nov. 14, 1997; pp. 521–530; vol. 91.

Kiefer, Michael, et al.; Ligand–affinity cloning and structure of a cell surface heparan sulfate proteoglycan that binds basic fibroblast growth factor; *Proc. Natl. Acad. Sci. USA;* Sep. 1990; pp. 6985–6989; vol. 87.

Liao, Fang, et al.; STRL22 Is a Receptor for the CC Chemokine MIP–3α; *Biochemical and Biophysical Research Communications;* 1997: pp. 212–217; vol. 236.

Nuttall, Stewart D., et al.; Design and Expression of Soluble CTLA–4 Variable Domain as a Scaffold for the Display of Functional Polypeptides; *Proteins: Structure, Function and Genetics;* 1999; pp. 217–227; vol. 36.

Power, Christine A., et al.; Cloning and Characterization of a Specific Receptor for the Novel CC Chemokine MIP–3α from Lung Dendritic Cells; *J. Exp. Med.;* Sep. 15, 1997; pp. 825–835; vol. 186, No. 6.

Roos, Regula Stuber, et al.; Identification of CCR8, the Receptor for the Human CC Chemokine I–309; *The Journal of Biological Chemistry;* Jul. 11, 1997; pp. 17251–17254; vol. 272, No. 28.

Rousch, Mat, et al.; Somatostatin displayed on filamentous phage as a receptor–specific agonist; *British Journal of Pharmacology;* 1998; pp. 5–16; vol. 125.

Rucker, Joseph, et al.; Utilization of Chemokine Receptors, Orphan Receptors, and Herpesvirus–Encoded Receptors by Diverse Human and Simian Immunodeficiency Viruses: *Journal of Virology;* Dec. 1997; pp. 8999–9007; vol. 71, No. 12.

Schall, Thomas J.; Novel Technology for the Identification of Specific Inhibitors of Orphan Chemokine Receptors (abstract); Book of Abstracts from the American Chemical Society National Meeting; San Francisco, CA; Mar. 26–30, 2000; No. 339.

Smith, W. Clay, et al.; (Identification of Regions of Arrestin That Bind to Rhodopsin; *Biochemistry,* 1999; pp. 2752–2761; vol. 38.

Souriau, Christelle, et al.; Direct Selection of EGF Mutants Displayed on Filamentous Phage Using Cells Overexpressing EGF Receptor; *Biol. Chem.;* Apr. 1999; pp. 451–458; vol. 380.

Szardenings, Michael, et al; Phage Display Selection on Whole Cells Yields a Peptide Specific for Melanocortin Receptor 1; *The Journal of Biological Chemistry;* Oct. 31, 1997; pp. 27943–27948; vol. 272, No. 44.

Takaki, Satoshi, et al.; Molecular cloning and expression of the murine interleukin–5 receptor; *The EMBO Journal;* 1990; pp. 4367–4374; vol. 9, No. 13.

Tang, Xiao–Bo, et al.; Construction of Transforming Growth Factor Alpha (TGF–α) Phage Library and Identification of High Binders of Epidermal Growth Factor Receptor (EGFR) by Phage Display; *J. Biochem;* 1997; pp. 686–690; vol. 122, No. 4.

Tiffany, H. Lee, et al.; Identification of CCR8: A Human Monocyte and Thymus Receptor for the CC Chemokine I–309; *the Journal of Experimental Medicine;* Jul. 7, 1997; pp. 165–170; vol. 186, No. 1.

Williams, Christopher; Biotechnology match making: screening orphan ligands and receptors; *Current Opinion in Biotechnology;* 2000; pp. 42–46; vol. 11.

Xie, Guo–Xi, et al.; Expression cloning of cDNA encoding a seven–helix receptor from human placenta with affinity for opioid ligands; *Proc. Natl. Acad. Sci. USA;* May 1992; pp. 4124–4128; vol. 89.

Xingping, Liu, et al.; Specific Binding of Human Bone Morphogenetic Protein (2A) with Mouse Osteoblastic Cells; *Chinese Medical Sciences Journal;* Jun. 1996; pp. 97–99; vol. 11, No. 2.

Yoshida, Ryu, et al; Molecular Cloning of a Novel Human CC Chemokine EBI1–ligand Chemokine That Is a Specific Functional Ligand for EBI1, CCR7, *The Journal of Biological Chemistry;*; May 23, 1997; pp. 13803–13809.

Yoshida, Ryu, et al.; Identification of Single C Motif–1/Lymphotactin Receptor XCR1; *The Journal of Biological Chemistry;* Jun. 26, 1998; pp. 16551–16554; vol. 273, No. 26.

Zaballos, Angel, et al.; Cutting Edge; Identification of the Orphan Chemokine Receptor GPR–9–6 as CCR9, the Receptor for the Chemokine TECK; *The Journal of Immunology;* 1999; pp. 5671–5675.

copy of International Search Report for PCT/US 00/34503.

```
ATGGCTTTGG AACAGAACCA GTCAACAGAT TATTATTATG AGGAAAATGA        50
 M  A  L  E   Q  N  Q   S  T  D    Y  Y  Y  E   E  N  E

AATGAATGGC ACTTATGACT ACAGTCAATA TGAACTGATC TGTATCAAAG       100
 M  N  G   T  Y  D  Y  T  V  N    M  N  *   L  Y  Q  S

AAGATGTCAG AGAATTTGCA AAAGTTTTCC TCCCTGTATT CCTCACAATA       150
 D  V  R    E  F  A    K  V  F  L  P  V  F   L  T  I

GTTTTCGTCA TTGGACTTGC AGGCAATTCC ATGGTAGTGG CAATTTATGC       200
 V  F  V  I  G  L  A   G  N  S   M  V  V  A   I  Y  A

CTATTACAAG AAACAGAGAA CCAAAACAGA TGTGTACATC CTGAATTTGG       250
 Y  Y  K    K  Q  R  T  K  T  D   V  Y  I    L  N  L  A

CTGTAGCAGA TTTACTCCTT CTATTCACTC TGCCTTTTTG GGCTGTTAAT       300
 V  A  D    L  L  L    L  F  T  L  P  F  W   A  V  N

GCAGTTCATG GGTGGGTTTT AGGGAAAATA ATGTGCAAAA TAACTTCAGC       350
 A  V  H  G  W  V  L   G  K  I   M  C  K  I  T  S  A

CTTGTACACA CTAAACTTTG TCTCTGGAAT GCAGTTTCTG GCTTGTATCA       400
 L  Y  T    L  N  F  V  S  G  M   Q  F  L   A  C  I  S

GCATAGACAG ATATGTGGCA GTAACTAAAG TCCCCAGCCA ATCAGGAGTG       450
 I  D  R    Y  V  A    V  T  K  V  P  S  Q   S  G  V

GGAAAACCAT GCTGGATCAT CTGTTTCTGT GTCTGGATGG CTGCCATCTT       500
 G  K  P  C  W  I  I   C  F  C    V  W  M  A  A  I  L

GCTGAGCATA CCCCAGCTGG TTTTTTATAC AGTAAATGAC AATGCTAGGT       550
 L  S  I    P  Q  L  V  F  Y  T   V  N  D    N  A  R  C

GCATTCCCAT TTTCCCCCGC TACCTAGGAA CATCAATGAA AGCATTGATT       600
 I  P  I    F  P  R    Y  L  G  T  S  M  K   A  L  I

CAAATGCTAG AGATCTGCAT TGGATTTGTA GTACCCTTTC TTATTATGGG       650
 Q  M  L  E  I  C  I   G  F  V    V  P  F  L  I  M  G

GGTGTGCTAC TTTATCACAG CAAGGACACT CATGAAGATG CCAAACATTA       700
 V  C  Y    F  I  T  A  R  T  L   M  K  M    P  N  I  K

AAATATCTCG ACCCCTAAAA GTTCTGCTCA CAGTCGTTAT AGTTTTCATT       750
 I  S  R    P  L  K    V  L  L  T  V  V  I   V  F  I

GTCACTCAAC TGCCTTATAA CATTGTCAAG TTCTGCCGAG CCATAGACAT       800
 V  T  Q  L  P  Y  N   I  V  K    F  C  R  A  I  D  I

CATCTACTCC CTGATCACCA GCTGCAACAT GAGCAAACGC ATGGACATCG       850
 I  Y  S    L  I  T  S  C  N  M   S  K  R    M  D  I  A

CCATCCAAGT CACAGAAAGC ATCGCACTCT TCACAGCTG CCTCAACCCA        900
 I  Q  V    T  E  S    I  A  L  F  H  S  C   L  N  P

ATCCTTTATG TTTTTATGGG AGCATCTTTC AAAAACTACG TTATGAAAGT       950
 I  L  Y  V  F  M  G   A  S  F    K  N  Y  V  M  K  V

GGCCAAGAAA TATGGGTCCT GGAGAAGACA GAGACAAAGT GTGGAGGAGT      1000
 A  K  K    Y  G  S  W  R  R  Q   R  Q  S    V  E  E  F

TTCCTTTTGA TTCTGAGGGT CCTACAGAGC CAACCAGTAC TTTTAGCATT      1050
 P  F  D    S  E  G    P  T  E  P  T  S  T   F  S  I

TAAAGGTAAA ACTGCTCTGC CTTTTGCTTG GATACATATG AATGATGCTT      1100

TCCCCTCAAA TAAAACATCT GCCTTATTCT GAAAAAAAAA AAAAAM         1147
```

FIG. 2

SEQUENCE LISTING

```
<160> NUMBER OF SEQ ID NOS: 103

<210> SEQ ID NO 1
<211> LENGTH: 1147
<212> TYPE: DNA
<213> ORGANISM: Homo sapiens
<220> FEATURE:
<223> OTHER INFORMATION: human CCR10
<221> NAME/KEY: CDS
<222> LOCATION: ()..(1053)

<400> SEQUENCE: 1 atg gct ttg gaa cag aac cag tca aca gat tat tat tat gag gaa aat      48
```

```
Met Ala Leu Glu Gln Asn Gln Ser Thr Asp Tyr Tyr Tyr Glu Glu Asn
  1               5                  10                  15 gaa atg aat ggc act tat gac tac agt caa tat gaa ctg atc tgt atc        96
Glu Met Asn Gly Thr Tyr Asp Tyr Ser Gln Tyr Glu Leu Ile Cys Ile
                 20                  25                  30 aaa gaa gat gtc aga gaa ttt gca aaa gtt ttc ctc cct gta ttc ctc       144
Lys Glu Asp Val Arg Glu Phe Ala Lys Val Phe Leu Pro Val Phe Leu
             35                  40                  45 aca ata gtt ttc gtc att gga ctt gca ggc aat tcc atg gta gtg gca       192
Thr Ile Val Phe Val Ile Gly Leu Ala Gly Asn Ser Met Val Val Ala
         50                  55                  60 att tat gcc tat tac aag aaa cag aga acc aaa aca gat gtg tac atc       240
Ile Tyr Ala Tyr Tyr Lys Lys Gln Arg Thr Lys Thr Asp Val Tyr Ile
 65                  70                  75                  80 ctg aat ttg gct gta gca gat tta ctc ctt cta ttc act ctg cct ttt       288
Leu Asn Leu Ala Val Ala Asp Leu Leu Leu Leu Phe Thr Leu Pro Phe
                 85                  90                  95 tgg gct gtt aat gca gtt cat ggg tgg gtt tta ggg aaa ata atg tgc       336
Trp Ala Val Asn Ala Val His Gly Trp Val Leu Gly Lys Ile Met Cys
             100                 105                 110 aaa ata act tca gcc ttg tac aca cta aac ttt gtc tct gga atg cag       384
Lys Ile Thr Ser Ala Leu Tyr Thr Leu Asn Phe Val Ser Gly Met Gln
         115                 120                 125 ttt ctg gct tgt atc agc ata gac aga tat gtg gca gta act aaa gtc       432
Phe Leu Ala Cys Ile Ser Ile Asp Arg Tyr Val Ala Val Thr Lys Val
     130                 135                 140 ccc agc caa tca gga gtg gga aaa cca tgc tgg atc atc tgt ttc tgt       480
Pro Ser Gln Ser Gly Val Gly Lys Pro Cys Trp Ile Ile Cys Phe Cys
145                 150                 155                 160 gtc tgg atg gct gcc atc ttg ctg agc ata ccc cag ctg gtt ttt tat       528
Val Trp Met Ala Ala Ile Leu Leu Ser Ile Pro Gln Leu Val Phe Tyr
                 165                 170                 175 aca gta aat gac aat gct agg tgc att ccc att ttc ccc cgc tac cta       576
Thr Val Asn Asp Asn Ala Arg Cys Ile Pro Ile Phe Pro Arg Tyr Leu
             180                 185                 190 gga aca tca atg aaa gca ttg att caa atg cta gag atc tgc att gga       624
Gly Thr Ser Met Lys Ala Leu Ile Gln Met Leu Glu Ile Cys Ile Gly
         195                 200                 205 ttt gta gta ccc ttt ctt att atg ggg gtg tgc tac ttt atc aca gca       672
Phe Val Val Pro Phe Leu Ile Met Gly Val Cys Tyr Phe Ile Thr Ala
     210                 215                 220 agg aca ctc atg aag atg cca aac att aaa ata tct cga ccc cta aaa       720
Arg Thr Leu Met Lys Met Pro Asn Ile Lys Ile Ser Arg Pro Leu Lys
225                 230                 235                 240 gtt ctg ctc aca gtc gtt ata gtt ttc att gtc act caa ctg cct tat       768
Val Leu Leu Thr Val Val Ile Val Phe Ile Val Thr Gln Leu Pro Tyr
                 245                 250                 255 aac att gtc aag ttc tgc cga gcc ata gac atc atc tac tcc ctg atc       816
Asn Ile Val Lys Phe Cys Arg Ala Ile Asp Ile Ile Tyr Ser Leu Ile
             260                 265                 270 acc agc tgc aac atg agc aaa cgc atg gac atc gcc atc caa gtc aca       864
Thr Ser Cys Asn Met Ser Lys Arg Met Asp Ile Ala Ile Gln Val Thr
         275                 280                 285 gaa agc atc gca ctc ttt cac agc tgc ctc aac cca atc ctt tat gtt       912
Glu Ser Ile Ala Leu Phe His Ser Cys Leu Asn Pro Ile Leu Tyr Val
     290                 295                 300 ttt atg gga gca tct ttc aaa aac tac gtt atg aaa gtg gcc aag aaa       960
Phe Met Gly Ala Ser Phe Lys Asn Tyr Val Met Lys Val Ala Lys Lys
305                 310                 315                 320
```

-continued

```
tat ggg tcc tgg aga aga cag aga caa agt gtg gag gag ttt cct ttt    1008
Tyr Gly Ser Trp Arg Arg Gln Arg Gln Ser Val Glu Glu Phe Pro Phe
            325                 330                 335 gat tct gag ggt cct aca gag cca acc agt act ttt agc att taa        1053
Asp Ser Glu Gly Pro Thr Glu Pro Thr Ser Thr Phe Ser Ile
        340                 345                 350 aggtaaaact gctctgcctt ttgcttggat acatatgaat gatgctttcc cctcaaataa  1113
aacatctgcc ttattctgaa aaaaaaaaaa aaam                              1147

<210> SEQ ID NO 2
<211> LENGTH: 350
<212> TYPE: PRT
<213> ORGANISM: Homo sapiens
<223> OTHER INFORMATION: human CCR10

<400> SEQUENCE: 2

Met Ala Leu Glu Gln Asn Gln Ser Thr Asp Tyr Tyr Tyr Glu Glu Asn
  1               5                  10                  15

Glu Met Asn Gly Thr Tyr Asp Tyr Ser Gln Tyr Glu Leu Ile Cys Ile
             20                  25                  30

Lys Glu Asp Val Arg Glu Phe Ala Lys Val Phe Leu Pro Val Phe Leu
         35                  40                  45

Thr Ile Val Phe Val Ile Gly Leu Ala Gly Asn Ser Met Val Val Ala
     50                  55                  60

Ile Tyr Ala Tyr Tyr Lys Lys Gln Arg Thr Lys Thr Asp Val Tyr Ile
 65                  70                  75                  80

Leu Asn Leu Ala Val Ala Asp Leu Leu Leu Phe Thr Leu Pro Phe
                 85                  90                  95

Trp Ala Val Asn Ala Val His Gly Trp Val Leu Gly Lys Ile Met Cys
                100                 105                 110

Lys Ile Thr Ser Ala Leu Tyr Thr Leu Asn Phe Val Ser Gly Met Gln
            115                 120                 125

Phe Leu Ala Cys Ile Ser Ile Asp Arg Tyr Val Ala Val Thr Lys Val
130                 135                 140

Pro Ser Gln Ser Gly Val Gly Lys Pro Cys Trp Ile Ile Cys Phe Cys
145                 150                 155                 160

Val Trp Met Ala Ala Ile Leu Leu Ser Ile Pro Gln Leu Val Phe Tyr
                165                 170                 175

Thr Val Asn Asp Asn Ala Arg Cys Ile Pro Ile Phe Pro Arg Tyr Leu
            180                 185                 190

Gly Thr Ser Met Lys Ala Leu Ile Gln Met Leu Glu Ile Cys Ile Gly
        195                 200                 205

Phe Val Val Pro Phe Leu Ile Met Gly Val Cys Tyr Phe Ile Thr Ala
    210                 215                 220

Arg Thr Leu Met Lys Met Pro Asn Ile Lys Ile Ser Arg Pro Leu Lys
225                 230                 235                 240

Val Leu Leu Thr Val Val Ile Val Phe Ile Val Thr Gln Leu Pro Tyr
                245                 250                 255

Asn Ile Val Lys Phe Cys Arg Ala Ile Asp Ile Ile Tyr Ser Leu Ile
            260                 265                 270

Thr Ser Cys Asn Met Ser Lys Arg Met Asp Ile Ala Ile Gln Val Thr
        275                 280                 285

Glu Ser Ile Ala Leu Phe His Ser Cys Leu Asn Pro Ile Leu Tyr Val
    290                 295                 300

Phe Met Gly Ala Ser Phe Lys Asn Tyr Val Met Lys Val Ala Lys Lys
```

```
                305                 310                 315                 320
Tyr Gly Ser Trp Arg Arg Gln Arg Gln Ser Val Glu Phe Pro Phe
                325                 330                 335
Asp Ser Glu Gly Pro Thr Glu Pro Thr Ser Thr Phe Ser Ile
                340                 345                 350

<210> SEQ ID NO 3
<211> LENGTH: 226
<212> TYPE: PRT
<213> ORGANISM: Homo sapiens
<220> FEATURE:
<223> OTHER INFORMATION: Fractalkine Mucin-Repeat Region

<400> SEQUENCE: 3

Ile Gly Glu Val Lys Pro Arg Thr Thr Pro Ala Ala Gly Gly Met Asp
 1               5                   10                  15

Glu Ser Val Val Leu Glu Pro Glu Ala Thr Gly Glu Ser Ser Ser Leu
                20                  25                  30

Glu Pro Thr Pro Ser Ser Gln Glu Ala Gln Arg Ala Leu Gly Thr Ser
            35                  40                  45

Pro Glu Leu Pro Thr Gly Val Thr Gly Ser Ser Gly Thr Arg Leu Pro
        50                  55                  60

Pro Thr Pro Lys Ala Gln Asp Gly Gly Pro Val Gly Thr Glu Leu Phe
 65                 70                  75                  80

Arg Val Pro Pro Val Ser Thr Ala Ala Thr Trp Gln Ser Ser Ala Pro
                85                  90                  95

His Gln Pro Gly Pro Ser Leu Trp Ala Glu Ala Lys Thr Ser Glu Ala
            100                 105                 110

Pro Ser Thr Gln Asp Pro Ser Thr Gln Ala Ser Thr Ala Ser Ser Pro
        115                 120                 125

Ala Pro Glu Glu Asn Ala Pro Ser Glu Gly Gln Arg Val Trp Gly Gln
    130                 135                 140

Gly Gln Ser Pro Arg Pro Glu Asn Ser Leu Glu Arg Glu Glu Met Gly
145                 150                 155                 160

Pro Val Pro Ala His Thr Asp Ala Phe Gln Asp Trp Gly Pro Gly Ser
                165                 170                 175

Met Ala His Val Ser Val Val Pro Val Ser Ser Glu Gly Thr Pro Ser
            180                 185                 190

Arg Glu Pro Val Ala Ser Gly Ser Trp Thr Pro Lys Ala Glu Glu Pro
        195                 200                 205

Ile His Ala Thr Met Asp Pro Gln Arg Leu Gly Val Leu Ile Thr Pro
    210                 215                 220

Val Pro
225

<210> SEQ ID NO 4
<211> LENGTH: 237
<212> TYPE: PRT
<213> ORGANISM: Homo sapiens
<220> FEATURE:
<223> OTHER INFORMATION: Fractalkine Mucin-Repeat Sequence Residues 100-
      336

<400> SEQUENCE: 4

Gly Gly Thr Phe Glu Lys Gln Ile Gly Glu Val Lys Pro Arg Thr Thr
 1               5                   10                  15

Pro Ala Ala Gly Gly Met Asp Glu Ser Val Val Leu Glu Pro Glu Ala
                20                  25                  30
```

```
Thr Gly Glu Ser Ser Ser Leu Glu Pro Thr Pro Ser Ser Gln Glu Ala
        35                  40                  45

Gln Arg Ala Leu Gly Thr Ser Pro Glu Leu Pro Thr Gly Val Thr Gly
        50                  55                  60

Ser Ser Gly Thr Arg Leu Pro Pro Thr Pro Lys Ala Gln Asp Gly Gly
65                  70                  75                  80

Pro Val Gly Thr Glu Leu Phe Arg Val Pro Pro Val Ser Thr Ala Ala
                    85                  90                  95

Thr Trp Gln Ser Ser Ala Pro His Gln Pro Gly Pro Ser Leu Trp Ala
                100                 105                 110

Glu Ala Lys Thr Ser Glu Ala Pro Ser Thr Gln Asp Pro Ser Thr Gln
                115                 120                 125

Ala Ser Thr Ala Ser Ser Pro Ala Pro Glu Glu Asn Ala Pro Ser Glu
                130                 135                 140

Gly Gln Arg Val Trp Gly Gln Gly Gln Ser Pro Arg Pro Glu Asn Ser
145                 150                 155                 160

Leu Glu Arg Glu Glu Met Gly Pro Val Pro Ala His Thr Asp Ala Phe
                165                 170                 175

Gln Asp Trp Gly Pro Gly Ser Met Ala His Val Ser Val Val Pro Val
                180                 185                 190

Ser Ser Glu Gly Thr Pro Ser Arg Glu Pro Val Ala Ser Gly Ser Trp
                195                 200                 205

Thr Pro Lys Ala Glu Glu Pro Ile His Ala Thr Met Asp Pro Gln Arg
        210                 215                 220

Leu Gly Val Leu Ile Thr Pro Val Pro Asp Ala Gln Ala
225                 230                 235

<210> SEQ ID NO 5
<211> LENGTH: 10
<212> TYPE: PRT
<213> ORGANISM: Homo sapiens
<220> FEATURE:
<223> OTHER INFORMATION: Mucin Repeat Domain

<400> SEQUENCE: 5

Ile Gly Glu Val Lys Pro Arg Thr Thr Pro
1               5                   10

<210> SEQ ID NO 6
<211> LENGTH: 11
<212> TYPE: PRT
<213> ORGANISM: Homo sapiens
<220> FEATURE:
<223> OTHER INFORMATION: Mucin Repeat Domain

<400> SEQUENCE: 6

Gly Gly Met Asp Glu Ser Val Val Leu Glu Pro
1               5                   10

<210> SEQ ID NO 7
<211> LENGTH: 11
<212> TYPE: PRT
<213> ORGANISM: Homo sapiens
<220> FEATURE:
<223> OTHER INFORMATION: Mucin Repeat Domain

<400> SEQUENCE: 7

Thr Gly Glu Ser Ser Ser Leu Glu Pro Thr Pro
1               5                   10
```

```
<210> SEQ ID NO 8
<211> LENGTH: 10
<212> TYPE: PRT
<213> ORGANISM: Homo sapiens
<220> FEATURE:
<223> OTHER INFORMATION: Mucin Repeat Domain

<400> SEQUENCE: 8

Leu Gly Thr Ser Pro Glu Leu Pro Thr Gly
 1               5                  10

<210> SEQ ID NO 9
<211> LENGTH: 12
<212> TYPE: PRT
<213> ORGANISM: Homo sapiens
<220> FEATURE:
<223> OTHER INFORMATION: Mucin Repeat Domain

<400> SEQUENCE: 9

Thr Gly Ser Ser Gly Thr Arg Leu Pro Pro Thr Pro
 1               5                  10

<210> SEQ ID NO 10
<211> LENGTH: 12
<212> TYPE: PRT
<213> ORGANISM: Homo sapiens
<220> FEATURE:
<223> OTHER INFORMATION: Mucin Repeat Domain

<400> SEQUENCE: 10

Val Gly Thr Glu Leu Phe Arg Val Pro Pro Val Ser
 1               5                  10

<210> SEQ ID NO 11
<211> LENGTH: 11
<212> TYPE: PRT
<213> ORGANISM: Homo sapiens
<220> FEATURE:
<223> OTHER INFORMATION: Mucin Repeat Domain

<400> SEQUENCE: 11

Ala Ala Thr Trp Gln Ser Ser Ala Pro His Gln
 1               5                  10

<210> SEQ ID NO 12
<211> LENGTH: 12
<212> TYPE: PRT
<213> ORGANISM: Homo sapiens
<220> FEATURE:
<223> OTHER INFORMATION: Mucin Repeat Domain

<400> SEQUENCE: 12

Pro Gly Pro Ser Leu Trp Ala Glu Ala Lys Thr Ser
 1               5                  10

<210> SEQ ID NO 13
<211> LENGTH: 10
<212> TYPE: PRT
<213> ORGANISM: Homo sapiens
<220> FEATURE:
<223> OTHER INFORMATION: Mucin Repeat Domain

<400> SEQUENCE: 13

Glu Ala Pro Ser Thr Gln Asp Pro Ser Thr
 1               5                  10
```

```
<210> SEQ ID NO 14
<211> LENGTH: 10
<212> TYPE: PRT
<213> ORGANISM: Homo sapiens
<220> FEATURE:
<223> OTHER INFORMATION: Mucin Repeat Domain

<400> SEQUENCE: 14

Gln Ala Ser Thr Ala Ser Ser Pro Ala Pro
 1               5                  10

<210> SEQ ID NO 15
<211> LENGTH: 10
<212> TYPE: PRT
<213> ORGANISM: Homo sapiens
<220> FEATURE:
<223> OTHER INFORMATION: Mucin Repeat Domain

<400> SEQUENCE: 15

Val Trp Gly Gln Gly Gln Ser Pro Arg Pro
 1               5                  10

<210> SEQ ID NO 16
<211> LENGTH: 11
<212> TYPE: PRT
<213> ORGANISM: Homo sapiens
<220> FEATURE:
<223> OTHER INFORMATION: Mucin Repeat Domain

<400> SEQUENCE: 16

Ser Leu Glu Arg Glu Glu Met Gly Pro Val Pro
 1               5                  10

<210> SEQ ID NO 17
<211> LENGTH: 10
<212> TYPE: PRT
<213> ORGANISM: Homo sapiens
<220> FEATURE:
<223> OTHER INFORMATION: Mucin Repeat Domain
<223> OTHER INFORMATION: Mucin Repeat Domain

<400> SEQUENCE: 17

Ala His Thr Asp Ala Phe Gln Asp Trp Gly
 1               5                  10

<210> SEQ ID NO 18
<211> LENGTH: 11
<212> TYPE: PRT
<213> ORGANISM: Homo sapiens
<220> FEATURE:
<223> OTHER INFORMATION: Mucin Repeat Domain

<400> SEQUENCE: 18

Pro Gly Ser Met Ala His Val Ser Val Val Pro
 1               5                  10

<210> SEQ ID NO 19
<211> LENGTH: 10
<212> TYPE: PRT
<213> ORGANISM: Homo sapiens
<220> FEATURE:
<223> OTHER INFORMATION: Mucin Repeat Domain

<400> SEQUENCE: 19

Glu Gly Thr Pro Ser Arg Glu Pro Val Ala
 1               5                  10
```

-continued

<210> SEQ ID NO 20
<211> LENGTH: 11
<212> TYPE: PRT
<213> ORGANISM: Homo sapiens
<220> FEATURE:
<223> OTHER INFORMATION: Mucin Repeat Domain

<400> SEQUENCE: 20

```
Ser Gly Ser Trp Thr Pro Lys Ala Glu Glu Pro
  1               5                  10
```

<210> SEQ ID NO 21
<211> LENGTH: 11
<212> TYPE: PRT
<213> ORGANISM: Homo sapiens
<220> FEATURE:
<223> OTHER INFORMATION: Mucin Repeat Domain

<400> SEQUENCE: 21

```
Gln Arg Leu Gly Val Leu Ile Thr Pro Val Pro
  1               5                  10
```

<210> SEQ ID NO 22
<211> LENGTH: 55
<212> TYPE: PRT
<213> ORGANISM: Influenza virus
<220> FEATURE:
<223> OTHER INFORMATION: Hypervariable stalk region (amino acids 36-90)
of neuraminidase protein

<400> SEQUENCE: 22

```
His Phe Lys Gln Tyr Glu Cys Ser Ser Pro Pro Asn Asn Gln Val Ile
  1               5                  10                  15

Pro Cys Gln Pro Thr Ile Ile Glu Arg Asn Ile Thr Glu Ile Val Tyr
             20                  25                  30

Leu Thr Asn Thr Thr Ile Glu Lys Glu Ile Cys Pro Lys Leu Val Glu
         35                  40                  45

Tyr Arg Asn Trp Ser Lys Pro
     50                  55
```

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 23

```
ggtgaattca tggctcgcct acagactgc                                         29
```

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence:PCR Primer

<400> SEQUENCE: 24

```
ggtgaattct tggctcagct tattgagaat ca                                     32
```

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 25
ggtgaattca tgaagatctc cgtggctgcc                                    30

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence:PCR Primer

<400> SEQUENCE: 26
ggtgaattcg ttctccttca tgtccttgat atag                               34

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 27
ggtgaattca tggctcagtc actggctctg                                    30

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 28
ggtgaattct ggcccctttag gggtctgtg                                     29

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence:PCR Primer

<400> SEQUENCE: 29
ggtgaattca tgaagaaaag tggtgttctt ttcc                               34

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 30
ggtgaattct gtagtcttct tttgacgaga acg                                33

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 31
ggtgaattca tgaatcaaac tgcgattctg a                                  31

<210> SEQ ID NO 32

<211> LENGTH: 34
<212> TYPE: DNA
<213> ORGANISM: Artificial Sequence
<220> FEATURE:
<223> OTHER INFORMATION: Description of Artificial Sequence:PCR Primer

<400> SEQUENCE: 32
ggtgaattca ggagatcttt tagacatttc cttg                             34

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 33
gtggaattca tgagtgtgaa gggcatggc                                   29

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence:PCR Primer

<400> SEQUENCE: 34
ggtgaattca aaattctttc tttcaacttt tttga                            35

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 35
ggtgaattca tgaaggtctc cgcagcactt c                                31

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 36
ggtgaattct ggctttggag ttggagattt ttg                              33

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 37
ggtgaattca tggccccact gaagatgct                                   29

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 38
ggtgaattca gacctctcaa ggctttgcag                         30

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 39
ggtgaattca tgtgctgtac caagagtttg c                       31

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence:PCR Primer

<400> SEQUENCE: 40
ggtgaattcc atgttcttga cttttttact gagg                    34

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 41
ggtgaattca tggccctgct actggccct                          29

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 42
ggtgaattca ctgctgcggc gcttcatct                          29

<210> SEQ ID NO 43
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 43
ggtgaattca tgaacctgtg gctcctggc                          29

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 44
ggtgaattcc agtcctgaat tagctgatat cag                     33

<210> SEQ ID NO 45
<211> LENGTH: 29
<212> TYPE: DNA

```
<213> ORGANISM: Artificial Sequence
<220> FEATURE:
<223> OTHER INFORMATION: Description of Artificial Sequence:PCR Primer

<400> SEQUENCE: 45
ggtgaattca tgaagggcct tgcagctgc                                    29

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 46
ggtgaattcg gcattcagct tcaggtcgc                                    29

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 47
ggtgaattca tggctcagtc actggctctg                                   30

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 48
ggtgaattct ggccctttag gggtctgtg                                    29

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 49
ggtgaattca tgcagatcat caccacagcc c                                 31

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 50
ggtgaattct tttcttttg acgggcagtg c                                  31

<210> SEQ ID NO 51
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 51
ggtgaattca tgcaggtctc cactgctgc                                    29
```

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 52
ggtgaattcg gcactcagct ctaggtcgct                                    30

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 53
ggtgaattca tgaaagtctc tgcagtgctt ctg                                 33

<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence:PCR Primer

<400> SEQUENCE: 54
ggtgaattca gtcttcaggg tgtgagcttt cc                                  32

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 55
ggtgaattca tgaaagtctc tgccgcccctt                                    30

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 56
ggtgaattca gtcttcggag tttgggtttg c                                   31

<210> SEQ ID NO 57
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 57
ggtgaattca tgaaggtttc tgcagcgct                                      29

<210> SEQ ID NO 58
<211> LENGTH: 33
<212> TYPE: DNA
<213> ORGANISM: Artificial Sequence
<220> FEATURE:

```
<223> OTHER INFORMATION: Description of Artificial Sequence:PCR Primer

<400> SEQUENCE: 58
ggtgaattct ggcttcagat tttgaaatat ttg                           33

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence:PCR Primer

<400> SEQUENCE: 59
ggtgaattca tgaacgccaa ggtcgtgg                                 28

<210> SEQ ID NO 60
<211> LENGTH: 32
<212> TYPE: DNA
<213> ORGANISM: Artificial Sequence
<220> FEATURE:
<223> OTHER INFORMATION: Description of Artificial Sequence:PCR Primer

<400> SEQUENCE: 60
ggtgaattcc ttgtttaaag ctttctccag gt                            32

<210> SEQ ID NO 61
<211> LENGTH: 34
<212> TYPE: DNA
<213> ORGANISM: Artificial Sequence
<220> FEATURE:
<223> OTHER INFORMATION: Description of Artificial Sequence:PCR Primer

<400> SEQUENCE: 61
ggtgatatca tgaagatttc cacacttcta tgcc                          34

<210> SEQ ID NO 62
<211> LENGTH: 34
<212> TYPE: DNA
<213> ORGANISM: Artificial Sequence
<220> FEATURE:
<223> OTHER INFORMATION: Description of Artificial Sequence:PCR Primer

<400> SEQUENCE: 62
ggtgatatcg cctagacatg aaggttcaag gatg                          34

<210> SEQ ID NO 63
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 63
ggtgaattca tgaaggtctc cgtggctgc                                29

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 64
ggtgaattct attgagtagg gcttcagctt t                             31
```

<210> SEQ ID NO 65
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 65
ggtgaattca tgaaggtctt ctccttggtc atg                          33

<210> SEQ ID NO 66
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 66
ggtgaattcc gttgaggtgt tgctcagctt c                            31

<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence:PCR Primer

<400> SEQUENCE: 67
ggtgatatca tgaagtcatc tcgacatctc tg                           32

<210> SEQ ID NO 68
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 68
ggtgatatcg ggaatctttc tcttaaacac tgg                          33

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 69
ggtgaattca tgagctccgc agccgggttc                              30

<210> SEQ ID NO 70
<211> LENGTH: 36
<212> TYPE: DNA
<213> ORGANISM: Artificial Sequence
<220> FEATURE:
<223> OTHER INFORMATION: Description of Artificial Sequence:PCR Primer

<400> SEQUENCE: 70
ggtgaattca ctctccaaaa gtttcttaat tatttt                       36

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence:PCR Primer

<400> SEQUENCE: 71
ggtgaattca tgccaccctg cagctgtg                                        28

<210> SEQ ID NO 72
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 72
ggtgaattct aaagccattg tgaatatgat ctg                                  33

<210> SEQ ID NO 73
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 73
ggtcccggga tggcaggcct gatgaccat                                       29

<210> SEQ ID NO 74
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 74
ggtcccgggg caggtggttt ggttgccag                                       29

<210> SEQ ID NO 75
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 75
ggtgaatcca tgaagctctg cgtgactgtc c                                    31

<210> SEQ ID NO 76
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 76
ggtgaattcg ttcagttcca ggtcatacac gta                                  33

<210> SEQ ID NO 77
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 77
ggtgaattca tgaaggtctc cgtggctgc                                       29

<210> SEQ ID NO 78
<211> LENGTH: 31

```
<212> TYPE: DNA
<213> ORGANISM: Artificial Sequence
<220> FEATURE:
<223> OTHER INFORMATION: Description of Artificial Sequence:PCR Primer

<400> SEQUENCE: 78
ggtgaattca ttcttcctgg tcttgatccg t                                  31

<210> SEQ ID NO 79
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 79
ggtgaattca tgagaaactc caagactgcc a                                  31

<210> SEQ ID NO 80
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 80
ggtgaattca gcaatgacct tgttcccaga t                                  31

<210> SEQ ID NO 81
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 81
ggtgaattca tgatacttct catcctggcc c                                  31

<210> SEQ ID NO 82
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 82
ggtgaattcg ccagtcaggg tcacagctg                                     29

<210> SEQ ID NO 83
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 83
ggtgaattca tgaaggtctc cgaggctgc                                     29

<210> SEQ ID NO 84
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 84
```

```
ggtgaattcc tgggagttga ggagctggg                                29
```

<210> SEQ ID NO 85
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 85

```
ggtgaattca tgaagccttt tcatactgcc c                             31
```

<210> SEQ ID NO 86
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 86

```
ggtgaattct tgtttgtagg tccgtggttg t                             31
```

<210> SEQ ID NO 87
<211> LENGTH: 28
<212> TYPE: DNA
<213> ORGANISM: Artificial Sequence
<220> FEATURE:
<223> OTHER INFORMATION: Description of Artificial Sequence:PCR Primer

<400> SEQUENCE: 87

```
ggtgatatca tgacttccaa gctggccg                                 28
```

<210> SEQ ID NO 88
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 88

```
ggtgatatct gaattctcag ccctcttcaa a                             31
```

<210> SEQ ID NO 89
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 89

```
ggtgaattca tgagcctcct gtccagccg                                29
```

<210> SEQ ID NO 90
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 90

```
ggtgaattcg ttttccttgt ttccaccgtc c                             31
```

<210> SEQ ID NO 91
<211> LENGTH: 29
<212> TYPE: DNA
<213> ORGANISM: Artificial Sequence

```
<220> FEATURE:
<223> OTHER INFORMATION: Description of Artificial Sequence:PCR Primer

<400> SEQUENCE: 91
ggtgatatca tggcccacgc cacgctctc                                  29

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 92
ggtgatatcg ttggtgctcc ccttgttcag                                 30

<210> SEQ ID NO 93
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 93
ggtgatatca tgcccgcgc cacgctctc                                   29

<210> SEQ ID NO 94
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 94
ggtgatatcg ttggatttgc cattttcag c                                31

<210> SEQ ID NO 95
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 95
ggtgatatca tgagcctcag acttgatacc acc                             33

<210> SEQ ID NO 96
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 96
ggtgatatca tcagcagatt catcacctgc c                               31

<210> SEQ ID NO 97
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 97
ggtgatatca tggcccgcgc tgctctctc                                  29
```

```
<210> SEQ ID NO 98
<211> LENGTH: 34
<212> TYPE: DNA
<213> ORGANISM: Artificial Sequence
<220> FEATURE:
<223> OTHER INFORMATION: Description of Artificial Sequence:PCR Primer

<400> SEQUENCE: 98
ggtgatatcg ttggatttgt cactgttcag catc                              34

<210> SEQ ID NO 99
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 99
ggtgaattca tggcccccgt ccacgtttt                                    29

<210> SEQ ID NO 100
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 100
ggtgaattca tggacaccaa gggcatcct                                    29

<210> SEQ ID NO 101
<211> LENGTH: 11
<212> TYPE: PRT
<213> ORGANISM: Homo sapiens
<220> FEATURE:
<223> OTHER INFORMATION: translation of non-coding region of SEQ ID NO:1

<400> SEQUENCE: 101

Asn Cys Ser Ala Phe Cys Leu Asp Thr Tyr Glu
 1               5                  10

<210> SEQ ID NO 102
<211> LENGTH: 5
<212> TYPE: PRT
<213> ORGANISM: Homo sapiens
<220> FEATURE:
<223> OTHER INFORMATION: translation of non-coding region of SEQ ID NO:1

<400> SEQUENCE: 102

Cys Phe Pro Leu Lys
 1               5

<210> SEQ ID NO 103
<211> LENGTH: 11
<212> TYPE: PRT
<213> ORGANISM: Homo sapiens
<220> FEATURE:
<223> OTHER INFORMATION: translation of non-coding region of SEQ ID NO:1

<400> SEQUENCE: 103

Asn Ile Cys Leu Ile Leu Lys Lys Lys Lys
 1               5                  10
```

TETHERED LIGANDS AND METHODS OF USE

This application claims the benefit of U.S. Provisional Application No. 60/186,626, filed Mar. 3, 2000, the contents of which are incorporated by reference herein. This application also claims the benefit of U.S. Provisional Application No. 60/172,979 filed Dec. 20, 1999.

FIELD OF THE INVENTION

The invention relates to reagents and methods for characterizing receptor-ligand interactions, identifying modulators of such interactions, and characterizing the receptor expression profile of cells and cell populations. The invention finds application in the biomedical sciences.

BACKGROUND OF THE INVENTION

Communication between cells is a fundamental process involved in growth, differentiation, metabolism, and generation of biological responses (e.g., immune responses) in multicellular organisms. Often, cell-to-cell signaling is mediated by extracellular receptors or cell adhesion molecules. These membrane-associated molecules interact with other proteins, such as soluble factors such as peptide hormones, extracellular matrices, and cell surface molecules displayed by other cells. In some cases, signaling involves cell-to-cell contact (e.g., contact between two surface proteins on cells). An example of such an interaction is the binding of the T cell receptor on the surface of a T lymphocyte and the MHC/antigen complex on the surface of an antigen-presenting cell. A different type of cell-to-cell signaling is mediated by soluble polypeptides that, by interacting with a specific receptor on a target cell, lead to changes in target cell activity. An illustrative and important example cell-to-cell signaling mediated by soluble polypeptides is the activity of chemokines in mammalian systems.

Chemokines are a class of cytokines that play an important role in inflammatory responses, leukocyte trafficking, angiogenesis, and other biological processes related to the migration and activation of cells. As mediators of chemotaxis and inflammation, chemokines play roles in pathological conditions. For example, the concentration of chemokine MCP-1 is higher in the synovial fluid of patients suffering from rheumatoid arthritis than that of patients suffering from other arthritic diseases.

Known chemokines are typically assigned to one of four subfamilies based on the arrangement of cysteine motifs. In the so-called alpha-chemokines, for example, the first two of four cysteines (starting from the amino terminus) are separated by an intervening amino acid (i.e., having the motif C-X-C). The beta-chemokines are characterized by the absence of an intervening amino acid between first two cysteines (i.e., comprising the motif C—C). The smaller gamma-chemokine family is characterized by a single C residue (gamma). The delta-chemokine family is characterized by a pair of cysteines separated by three residues (i.e., having the motif $CX_3C$). The sole CX3C chemokine (fractalkine) is a type 1 membrane protein containing a chemokine domain tethered on a long mucin-like stalk. Fractalkine, also named neurotactin, has contains a chemokine domain at the amino terminus tethered on a long mucin-like stalk. For a recent review on chemokines, see Ward et al., 1998, *Immunity* 9:1–11 and Baggiolini et al., 1998, *Nature* 392:565–568, and the references cited therein.

Some chemokine activities (e.g., promigratory effects) are mediated by binding to an array of cell surface receptors on the surface of target leukocytes. These receptors are of the seven transmembrane spanning, G protein coupled receptor class (alternately referred to as 7TM or GPCR). Several seven-transmembrane-domain G protein-coupled receptors for C—C chemokines have been cloned: a C—C chemokine receptor-1 which recognizes MIP-1α, RANTES, MCP-2, MCP-3, and MIP-5 (Neote et al., 1993, *Cell*, 72:415–415); CCR2 which is a receptor for MCP1, 2, 3 and 4 or 5; CCR3 which is a receptor for RANTES, MCP-2, 3, 4, MIP-5 and eotaxin; CCR5 which is a receptor for MIP-1α, MIP-1β and RANTES; CCR4 which is a receptor for CMDC or TARC; CCR6 which is a receptor for LARC; and CCR7 which is a receptor for SLC and MIP-3β (reviewed in Sallusto et al., 1998, *Immunol.* Today 19:568 and Ward et al., 1998, *Immunity* 9:1–11).

Due to the importance of interactions between receptors (such as chemokine receptors) and their ligands in biological function, a need exists for rapid and effective methods for the characterization of such interactions.

SUMMARY OF THE INVENTION

In one aspect the invention provides an assay device having a plurality of different immobilized tethered ligand fusion proteins organized in an array, where the ligand-stalk fusion proteins include a ligand domain and a stalk domain ("assay device"). In one embodiment, the ligand-stalk fusion proteins have a ligand domain, an intermediate stalk domain, and an immobilization domain ("assay device"). In an embodiment, the ligand domain and the stalk domain are not associated in a naturally occurring protein. In various embodiments, the immobilized tethered ligand fusion proteins include a mucin-derived stalk sequence, a fractalkine mucin repeat region sequence, and/or a ligand domain encoding a chemokine.

In another aspect, the invention provides a tethered ligand fusion protein, where the ligand domain is other than a chemokine sequence.

In another aspect, the invention provides a method for identifying an interaction between a receptor and a ligand by contacting a cell expressing a receptor or a ligand-binding portion thereof with an immobilized tethered ligand fusion protein and, detecting binding of the cell and the tethered ligand fusion protein, where binding of the cell to the fusion protein is correlated with an interaction between the receptor and the ligand corresponding to the ligand domain of the fusion protein. In an embodiment, the tethered ligand is immobilized on an assay device, supra. In various embodiments, the cell expresses a recombinant receptor (e.g., an orphan receptor). In an embodiment, the cell expresses a chemokine receptor. In one embodiment, an interaction between a receptor and more than one ligand is detected.

In another aspect, the invention provides a method for identifying a modulator of an interaction between a receptor and a ligand by contacting cells expressing the receptor or a ligand-binding portion thereof with an immobilized tethered ligand fusion protein in the absence of a test compound, and measuring binding of the cells to an immobilized tethered ligand fusion protein, contacting cells expressing the receptor or a ligand-binding portion thereof with an immobilized tethered ligand fusion protein in the presence of a test compound, and measuring binding of the cells to the immobilized tethered ligand fusion protein; and comparing the levels of binding, where decreased binding of cells in the presence of the test compound indicates that the test compound is an inhibitor of the interaction between the receptor and the ligand corresponding the ligand domain of said fusion protein, and where increased binding of cells in the presence of the test compound indicates that the test compound is an enhancer of the interaction between the receptor and the receptor and the ligand corresponding the ligand domain of the fusion protein. In an embodiment, the tethered ligand is immobilized on an assay device, supra. In one embodiment, the receptor is a chemokine receptor.

In another aspect, the invention provides a method for detecting a profile of receptor expression in cells in a population of cells by contacting the population of cells with an immobilized tethered ligand fusion protein and detecting binding of cells of the population to the tethered ligand fusion protein, where binding of a cell in the cell population to a tethered ligand fusion protein is correlated with expression of a receptor that binds the ligand corresponding to the ligand domain of the fusion protein. In an embodiment, the tethered ligand is immobilized on an assay device, supra. In an embodiment, the contacting step involves contacting the population with a plurality of different fusion proteins and the detecting step involves detecting binding of cells to zero, one or more than one fusion proteins. In one embodiment, the population is heterogeneous, e.g., the population is obtained from synovial fluid, cerebral-spinal fluid, bronchial alveolar lavage (BAL) fluid, or blood. In an embodiment, the method includes quantitating the level of binding to each tethered ligand fusion protein in the array, or characterizing the cells bound at each sector of the array (e.g., by immunostaining).

In another aspect, the invention provides a method for diagnosis. The method includes the steps of obtaining a population of cells from a patient suspected of suffering from a disease, determining a receptor profile for the population, and, comparing said receptor profile with a profile characteristic of the disease state. In one embodiment the receptor profile is determined by contacting the population of cells with an immobilized tethered ligand fusion protein and identifying a tethered ligand fusion protein bound by cells of said population thereby identifying a receptor profile. In an embodiment, the tethered ligand is immobilized on an assay device, supra. In various embodiments, determining the method also includes quantitating the binding of cells at each sector of the array or characterizing the cells bound at each sector of the array, e.g., by immunostaining. In various embodiments, the disease is an inflammatory or allergic disease, or an autoimmune disease. In various embodiments, the population is obtained from synovial fluid, cerebral-spinal fluid, bronchial alveolar lavage (BAL) fluid, or blood.

In another aspect, the invention provides a method for detecting an effect of a drug or treatment on a patient by determining the receptor profile of a population of cells from the patient for the first time, administering the drug or treatment to the patient, determining the receptor profile of a population of cells from the patient for a second time, and comparing the receptor profiles obtained to determine the effect of the drug or treatment receptor-expressing cells in the patient. In an embodiment, the determining is carried out by contacting said population of cells with an immobilized tethered ligand fusion protein and identifying a subset of arrayed tethered ligand fusion proteins bound by cells of said population thereby identifying a receptor profile. In an embodiment, the tethered ligand is immobilized on an assay device, supra. In various embodiments, determining the method also includes quantitating the binding of cells at each sector of the array or characterizing the cells bound at each sector of the array, e.g., by immunostaining. In various embodiments, the population is obtained from synovial fluid, cerebral-spinal fluid, bronchial alveolar lavage (BAL) fluid, or blood.

In another aspect, the invention provides a method for identifying a modulator of an interaction between a receptor and a ligand by contacting cells expressing the receptor or a ligand-binding portion thereof with an immobilized tethered ligand fusion protein in the presence of a test compound and determining the level of binding to the fusion protein, contacting cells expressing the receptor or a ligand-binding portion thereof with the immobilized tethered ligand fusion protein in the absence of a test compound; and determining the level of binding to the fusion protein, and comparing the level of binding, where the ligand-stalk fusion proteins include a ligand domain, an intermediate stalk domain, and, an immobilization domain and where decreased binding of cells in the presence of the test compound indicates that the test compound is an inhibitor of the interaction between the receptor and the ligand corresponding the ligand domain of fusion protein, and where increased binding of cells in the presence of the test compound indicates that the test compound is an enhancer of the interaction between the receptor and the ligand corresponding the ligand domain of the fusion protein. In one embodiment, the ligand domain and the stalk domain are not associated in a naturally occurring protein. In an embodiment, the stalk domain is carboxy-terminal to the ligand domain, and the immobilization domain is carboxy-terminal to the stalk domain.

In another aspect, the invention provides the use of tethered ligand fusion proteins in any of the methods described herein.

BRIEF DESCRIPTION OF THE FIGURES

FIG. 2 shows the nucleotide sequence for a human CCR10 (SEQ ID NO:1), including translations of non-coding regions of the sequence (SEQ ID NOS:101–103), and the predicted amino acid sequence of the human CCR10 polypeptide (SEQ ID NO:2).

FIG. 3 shows the identification of CCR10 ligands by adhesion to stalkokines.

DETAILED DESCRIPTION

1. DEFINITIONS

Figure 1:
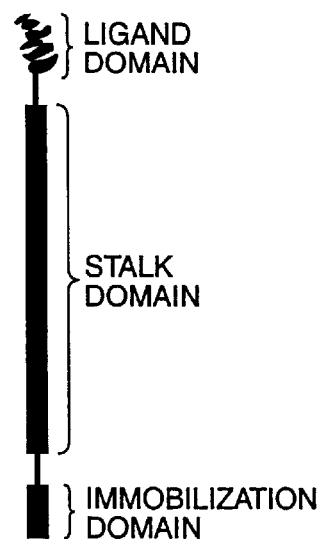
FIG. 1 shows the structure of a tethered ligand.

The following definitions are provided to assist the reader in the practice of the invention. As used herein:

The term "receptor" has the ordinary meaning in the art and refers to a protein that specifically binds a second protein. Usually (i.e., in some embodiments) receptors are membrane associated proteins characterized by a transmembrane domain, an extracellular domain and an intracellular domain. Such receptors are called "membrane associated receptors." In other embodiments, the term "receptor" is used to refer to other types of polypeptide binding proteins, e.g., adhesion molecules, soluble binding proteins. It will be apparent that, as used herein, the term "receptor" does not refer to immunoglobulins.

The term "ligand," refers to peptides or polypeptide that bind to a receptor protein. Typically, ligands are involved in cell-to-cell signaling or adhesion of cells to other cells or extracellular matrix.

The term "specific binding" refers to binding between two molecules, for example, a ligand and a receptor, characterized by the ability of a protein (ligand) to associate with another specific molecule (receptor) even in the presence of many other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay).

The term "orphan receptor" refers to a putative receptor polypeptide for which a naturally occurring cognate ligand is not known. Typically, orphan receptors are identified based on homology (sequence identity) to known receptors based on protein or gene sequence and structure.

The term "fusion protein," as used herein, refers to a composite polypeptide, i.e., a single contiguous amino acid sequence, made up of two or more (e.g., three) distinct polypeptides which are not normally fused together in a single amino acid sequence. Fusion proteins can generally be prepared using either recombinant nucleic acid methods, i.e., as a result of transcription and translation of a recombinant gene fusion product, which fusion comprises a segment encoding a first polypeptide region and a segment encoding a second polypeptide region, or by chemical synthesis methods well known in the art. Thus, for example, a single naturally occurring protein (e.g., Fractalkine) is not a fusion protein.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means (e.g., to increase expression of a receptor). The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. Transcription termination signals, enhancers, and other nucleic acid sequences that influence gene expression, can also be included in an expression cassette. An "expression vector" is a vector that contains the necessary elements for the transcription and translation of the inserted coding sequence required for the expression system employed (e.g., a vector containing an expression cassette).

A "recombinant polynucleotide" or a "recombinant polypeptide" is a non-naturally occurring polynucleotide or polypeptide that includes nucleic acid or amino acid sequences, respectively, from more than one source nucleic acid or polypeptide.

The term "chemokine" (abbreviated "CK") refers to a class of cytokines involved in inflammatory responses, leukocyte trafficking, angiogenesis, and other biological processes related to the migration and activation of cells. Known chemokines are typically assigned to one of four subfamilies ($\alpha$, $\beta$, $\gamma$, and $\delta$) based on the arrangement of cysteine motifs. A nonexhaustive list of chemokines is described in Table 2.

The term "receptor-bindable portion" when referring to a polypeptide ligand, refers to the portion of the ligand, often less than full-length naturally occurring protein) sufficient for binding to a cognate receptor (i.e., a receptor that binds the naturally occurring ligand).

2. INTRODUCTION

The present invention provides reagents, devices, and methods useful for analysis of protein-protein interactions such as receptor-ligand interactions. The invention provides reagents and methods for identification of modulators of such receptor-ligand interactions, and other methods, as described herein. In one embodiment, the invention is used to identify and characterize interactions between chemokines, e.g., human chemokines, and known or orphan chemokine receptors.

In an aspect of the invention, as described in detail infra, cells expressing receptors are contacted with one or more tethered ligands and specific binding, if present, is detected and analyzed. Such contacting, detection and analysis is sometimes referred to as "interrogation." The "tethered ligands" used according to the invention are fusion proteins having at least two, and usually at least three, distinct domains: a ligand domain, a stalk domain, and, optionally, an immobilization domain. The cells may be recombinant cells expressing a predefined receptor protein (including cells expressing an orphan receptor), or may be cells isolated from a biological source (such as a tissue from a patient or non-human animal).

Assays in which binding of a cell expressing a receptor and the tethered ligand fusion proteins of the invention is detected may be carried out in a variety of ways.

In one embodiment, the interaction between one or more tethered ligands and one or more receptor expressing cells is detected and characterized. In a particular, the effects of one or more test compound(s) on the interaction can be assayed.

For example, tethered ligand fusion protein of the invention (i.e., a single species) may be immobilized on a surface (e.g., a solid surface such as a slide, plate, bead, dipstick, or the like) and contacted with a test cell or cell population.

In another embodiment of the invention, a plurality (i.e., at least 3, typically at least 10, often at least 15) of different tethered ligands (i.e., having different ligand domains) are immobilized in an array. The array can be interrogated by recombinant cells expressing receptors known or suspected of specifically binding the ligand domain of a tethered ligand. The effect of test compounds on the interaction of the cells and tethered ligands of the array can be determined. The array can also be interrogated by populations of naturally occurring cells, and the receptor profile of the population determined (for diagnostic, screening, or other purposes). Notably, the tethered arrays of the invention are useful for determining the ligand binding profile of orphan receptors.

The invention finds use in the characterization of a variety of protein-protein interactions. In particular, the invention is useful for the characterization of interactions between 7-transmembrane receptors (e.g., chemokine receptors) and putative ligands (e.g., chemokines). However, as will be apparent infra, the invention is not limited to characterization of 7-transmembrane receptors.

3. TETHERED LIGANDS

As noted supra, the methods and devices of the invention make use of "tethered ligands." Tethered ligands are fusion proteins having a ligand domain, a stalk domain, and, usually, an immobilization domain. The stalk domain is positioned in between the ligand domain and the immobilization domain (i.e., it is "intermediate"). The stalk domain sequence may be contiguous with one or both of the other domains, but typically at least some additional (e.g., linker) sequences will be interposed. Typically, the ligand domain is located at the amino-terminus of the fusion protein, and the immobilization domain is at the carboxy-terminus (with the stalk domain in between). FIG. 1 shows a diagram of an exemplary tethered ligand.

In alternative embodiments, the ligand domain may be located at the carboxy-terminus of the fusion protein, and the immobilization domain at the amino-terminus. The latter orientation is useful when the ligand domain has the sequence of an intracellular protein, or intracellular domain of a transmembrane protein.

Techniques used in production of the tethered ligands of the invention (e.g., cloning and expression of recombinant proteins, including fusion proteins) are well known in the art and are described, for example, in Sambrook et al., 1989, Molecular Cloning: A Laboratory Manual, 2nd Ed., Vols. 1–3, Cold Spring Harbor Laboratory and Ausubel et al., Current Protocols In Molecular Biology, Greene Publishing and Wiley-lnterscience, New York, including 1999 and 2000 supplements. For example, it is understood that the various (e.g., at least 2) amino acid coding segments used to encode the fusion protein will be cloned in frame relative to each other, to encode the fusion protein.

The structure and production of tethered ligands will now be described in greater detail.

3.1 Ligand Domain

The ligand domain of tethered ligands has the sequence of a protein or peptide ligand of interest, which may be an extracellular ligand or an intracellular ligand.

Extracellular ligands are those polypeptide ligands that are naturally bound by extracellular domains of membrane associated receptors; exemplary extracellular ligands include chemokines (bound by chemokine receptors); other cytokines, interferon (bound by interferon receptors), dopamine (bound by dopamine receptors), Exemplary extracellular receptors are listed in Table 1, although many others will be apparent to those of skill. A particularly useful class of tethered ligands are those having a ligand domain corresponding to a chemokine. A tethered ligand having a chemokine domain is sometimes referred to as a "stalkokine," e.g., "TARC-stalkokine" for a tethered ligand having a TARC sequence in the ligand domain.

Chemokines and cytokines are well known in the art. Exemplary cytokines are listed in Table 2. References describing these and other cytokines are 10 provided in the R&D Systems Catalog (1999) and (2000) R&D Systems Inc., 614 McKinley Place N. E. MN 55413, the R&D online catalog at http:/www.mdsystems.com (e.g., Oct. 10, 1999), both of which are incorporated by reference for all purposes; the CFB (Cytokine Facts Book, 1994, Academic Press Ltd.), Chemokine Facts Book, 1997, Academic Press Ltd., incorporated by reference for all purposes, and the GenBank protein sequence database (http.//www.ncbi. nim.nih.gov/entrez/query.fcgi).

It will be appreciated that a ligand domain need not necessarily include the complete sequence of the intracellular or extracellular ligand to which it corresponds; in various embodiments, the ligand domain will comprise at least a receptor-bindable portion of the naturally occurring ligand.

TABLE 1

Exemplary Receptors

| Receptor Class | Subclasses & Examples | GenBank Accession Number |
|---|---|---|
| Chemokine Receptors | 1. CCR1 | NM001295 |
| | 2. CCR2 | NM000647 |
| | 3. CCR3 | NM001837 |
| | 4. CCR4 | AB023892 |
| | 5. CCR5 | NM000579 |
| | 6. CCR6 | NM004367 |
| | 7. CCR7 | NM001838 |
| | 8. CCR8 | NM005201 |
| | 9. CCR9 | NM006641 |
| | 10. CCR10 | AF233281 |
| | 11. CCR11 | NM016602 |

TABLE 1-continued

Exemplary Receptors

|   |   |   |   |
|---|---|---|---|
| 12. | CXCR1 (IL-8R alpha) | L19591 |
| 13. | CXCR2 (IL-8R beta) | NM001557 |
| 14. | CXCR3 GPR9 | NM001504 |
| 15. | CXCR4 | NM003467 |
| 16. | CXCR5 | AJ002211 |
| 17. | XCR1 | NM005283 |
| 18. | $CX_3CR1$ | U20350 |
| 19. | CMV US28 | L20501 |
| 20. | HHV8ORF74 | AF179931 |
| 21. | Duffy Ag | AF030521 |

Other Receptor Classes
Peptide
Angiotensin
Angiotensin type 1
Angiotensin type 2
Bombesin
Bradykinin
C5a anaphylatoxin
Fmet-leu-phe
Interleukin-8
Interleukin-8 type A
Interleukin-8 type B
Endothelin
Melanocortin
Melanocyte stimulating hormone
Adrenocorticotropic hormone
Melanocortin hormone
Neuropeptide Y
Neurotensin
Opioid
Opioid type D
Opioid type K
Opioid type M
Opioid type X
Somatostatin
Somatostatin type 1
Somatostatin type 2
Somatostatin type 3
Somatostatin type 4
Somatostatin type 5
Tachykinin
Substance P (NK1)
Substance K (NK2)
Neuromedin K (NK3)
Thrombin
Vasopressin-like
Vasopressin
Oxytocin
Galanin
Proteinase activated
Orexin
Chemokine/chemotactic factors like
Hormone protein
Follicle stimulating hormone
Lutropin-choriogonadotropic hormone
Thyrotropin
Viral
Class A Orphan/other
Burkitt's lymphoma receptor
Mas proto-oncogene
RDC1
EDG
GPR
RBS11
BONZO
Chemokine receptor-like 2
G10D
GP40 like
APJ like
Growth Factor Receptors
Hormone Receptors
Class I cytokine receptors
(hematopoietin family receptors
IL-6 (sharing gp 130)   IL-6
                        IL-11
                        CNTF
                        LIF

TABLE 1-continued

Exemplary Receptors

|   |   |
|---|---|
|  | Oncostatin M |
|  | Cardiotrophin 1 |
| GM-CSF (sharing β chain) | GM-CSF |
|  | IL-3 |
|  | IL-5 |
| IL-2 (sharing γ chain) | IL-2 |
|  | IL-4 |
|  | IL-7 |
|  | IL-9 |
|  | IL-15 |
| IL-13 (sharing α chain) | IL-13 |
|  | IL-14 |
|  | IL-12 |
|  | G-CSF |
|  | Erythropoietin |
|  | Growth hormone |
|  | Prolactin |
|  | IFN-α/β family |
|  | IFN-γ |
|  | IL-10 |
|  | TNF-α |
|  | TNF-β (LT-α) |
|  | LT-α/LT-β heteromes |
|  | NGF |
|  | Fas Ligand |
|  | CD40 ligand |
|  | TRAIL |
|  | IL-1α |
|  | IL-1β |
|  | IL-1 receptor antagonist |
|  | TGF-β |
|  | Bone morphogenetic proteins |

TABLE 2

Exemplary Cytokines

| | |
|---|---|
| 1. | TNF-alpha |
| 2. | CD27L |
| 3. | TGF-beta |
| 4. | TNF-beta |
| 5. | CD30L |
| 6. | IL-2 |
| 7. | VEGF (VEGF-A) |
| 8. | EGF |
| 9. | HB-EGF |
| 10. | IL-6 |
| 11. | SCF |
| 12. | BMPs |
| 13. | Lymphotoxin-beta |
| 14. | CD40L |
| 15. | IL-7 |
| 16. | VEGF-B |
| 17. | TGF-alpha |
| 18. | SMDF |
| 19. | LIF |
| 20. | Flt-3 Ligand |
| 21. | GDNFs |
| 22. | Fas Ligand |
| 23. | April |
| 24. | IL-9 |
| 25. | IL-3 |
| 26. | IL-1alpha |
| 27. | IFN-gamma |
| 28. | IGF-I |
| 29. | HGF |
| 30. | FGF-acidic |
| 31. | NGF |
| 32. | Thrombopoietin |
| 33. | PDGF-AA |
| 34. | VEGF-C |

TABLE 2-continued

Exemplary Cytokines

| | |
|---|---|
| 35. | Amphiregulin |
| 36. | IL-11 |
| 37. | Cardiotrophin-1 |
| 38. | M-CSF |
| 39. | Activins |
| 40. | TRAIL |
| 41. | TALL-1 |
| 42. | IL-15 |
| 43. | IL-5 |
| 44. | IL-1beta |
| 45. | IL-10 |
| 46. | IGF-II |
| 47. | MSP |
| 48. | FGF-basic |
| 49. | BDNF |
| 50. | Erythropoietin |
| 51. | PDGF-AB |
| 52. | VEGF-D |
| 53. | Betacellulin |
| 54. | G-CSF |
| 55. | CNTF |
| 56. | Midkine |
| 57. | Inhibins |
| 58. | TRANCE |
| 59. | 4-1BBL |
| 60. | IL-4 |
| 61. | GM-CSF |
| 62. | IL-18 |
| 63. | IL-17 |
| 64. | IL-16 |
| 65. | IL-12 |
| 66. | FGF-3-19 |
| 67. | Neurotrophins |
| 68. | Angiopoietins (1–4) |
| 69. | PDGF-BB |
| 70. | P1GF |
| 71. | Heregulins |
| 72. | Leptin |
| 73. | Oncostatin M |
| 74. | Pleiotrophin |
| 75. | MIS |
| 76. | LIGHT |
| 77. | OX40L |
| 78. | IL-13 |
| 79. | TWEAK |
| 80. | GITRL |
| 81. | Lymphotactin |
| 82. | BRAK |
| 83. | PARC |
| 84. | Eotaxin |
| 85. | Eotaxin-2 |
| 86. | MPIF-1 |
| 87. | HCC-1 |
| 88. | HCC-4 |
| 89. | SCYA26 |
| 90. | MIP-1alpha |
| 91. | MIP-1beta |
| 92. | MIP-1delta |
| 93. | I-309 |
| 94. | 6-Ckine |
| 95. | RANTES |
| 96. | MCP-1 |
| 97. | MCP-2 |
| 98. | MCP-3 |
| 99. | MCP-4 |
| 100. | TARC |
| 101. | MIP-3 alpha |
| 102. | MIP-3 beta |
| 103. | TECK |
| 104. | MDC |
| 105. | IL-8 |
| 106. | GCP-2 |
| 107. | MIG |
| 108. | SDF-1 |
| 109. | I-TAC |
| 110. | PF4 |
| 111. | ENA-78 |
| 112. | IP-10 |
| 113. | NAP-2 |
| 114. | GRO |
| 115. | BLC/BCA-1 |

In some alternative embodiments, the "receptor" is not the extracellular domain of a membrane associated receptor, but a different protein binding moiety, such as the protein-binding domain of an intracellular protein or protein domain. For example, the "receptor-ligand pair" used in the invention can be the intracellular domain of a CCR1 ("receptor") and a G-protein ("ligand"). In this case, the "ligand" is the G-protein domain and is expressed as a fusion protein with a stalk domain (e.g., a fractalkine mucin region sequence). The "receptor" is the intracellular domain of CCR1, that can be expressed as an amino-terminal fusion protein with a single transmembrane receptor (such as EGF receptor with a deleted kinase domain). This allows the CCR1 intracellular domain, for example, to be expressed extracellularly (i.e. on the surface of a cell). Thus, by immobilizing the G-protein tethered ligand onto a solid surface one can interrogate the cell expressing the CCR1 intracellular domain. Another example of an intracellular ligand (a protein that binds an intracellular protein, or intracellular protein domain), is a G protein that binds a G-protein coupled glutamate receptor.

3.2 Stalk Domain

The stalk domain of the tethered ligand fusion protein functions, in part, to display the ligand domain by elevating it a considerable distance above the substrate to which the tethered ligand fusion protein is immobilized. Without intending to be bound by a particular mechanism, it is believed that displaying the ligand a significant distance above the surface increases binding the ligand with the receptor displayed in receptor-expressing cells.

Typically, the length of the stalk domain of the fusion protein is at least about 50 amino acid residues at least about 75 amino acid residues, at least about 100 amino acid residues, often at least about 150 residues, and frequently at least about 200 residues. Typically, the stalk domain is between about 200 residues and 500 residues, and usually between about 200 residues and 300 residues. Generally, the ligand domain of the polypeptide is displayed at least about 20nm (e.g., between about 20 nm and about 60 nm), or at least about 30 nm away from (i.e., above) the surface to which the tethered ligand is immobilized. In embodiments, the ligand domain peptide is displayed at between around 30–40 nm above the surface. The measurement of the extension of the ligand domain is typically done by electron microscopy after heavy metal shadowing (see, e.g., Fong et al, 2000, *J Exp Med* 188:1413–19).

In addition to elevating the ligand domain away from the surface, the flexibility of the stalk region is believed to permit the ligand domain to adopt a variety of orientations, increasing the likelihood of a strong interaction with the receptor, and having unexpected advantages compared to other methods of immobilizing or displaying a ligand, such as standard ELISA. Typically, the stalk domain is selected to have sufficient rigidity to elevate the ligand but has flexibility to allow the ligand domain to adopt a variety of orientations.

In one embodiment, the stalk domain is derived from the fractalkine polypeptide (Bazan et al., 1997, *Nature*

385:640–644; See also, WO 97/27299). Fractalkine is a naturally occurring type 1 membrane protein containing a chemokine domain tethered on a long mucin-like stalk. Human fractalkine cDNA (Genbank Accession No. U84487) encodes a 397 residue membrane protein with a 24 residue predicted signal peptide, a 76 residue chemokine domain, a 241 residue stalk region containing 17 degenerate mucin-like repeats rich in motifs for O-glycosylated serine and threonine residues, a 19 residue transmembrane segment and a 37 residue cytoplasmic domain.

Thus, in exemplary embodiments, the stalk region has the sequence provided in Table 3A or 3B. In other embodiments, the stalk region includes at least one mucin repeat segment from a fractalkine stalk region, such as the human sequence shown in Table 4. In related embodiments, the stalk region has at least 10, at least 25, or at least 50 contiguous residues of a fractalkine stalk region, such as that shown in Table 3A or 3B, (e.g., subsequences or interactions thereof).

ecules that are heavily glycosylated and are expressed in epithelia of the respiratory, gastrointestinal, and reproductive tracts, e.g., MUC1 (GenBank accession number AF125525), MUC2 (L21998), MUC3 (AF113616), MUC4 (AJ000281), MUC5AC (U83139), MUC5B (AJ001402), MUC6 (U97698), MUC7 (L13283), MUC8 (U14383), MUC9 (oviductin) (AW271430). In other embodiments, the stalk domain has sequences from MAdCAM-1, GlyCAM-1, CD34 (See, e.g., Girard & Springer 1995; Van Klinken et al., 1988, *Anal Biochem* 265:103-16), consensus repeats from E-selectin, P- selectin, or L-selectin, or viral glycoprotein spikes (e.g., glycoproteins of viral origin, such as influenza, herpes simplex, human immunodeficiency, or Tobacco mosaic virus) In particular, the influenza virus neuraminidase protein (accession number 091744), and especially the hypervariable stalk region from amino acids 36 through 90 inclusive (i.e., comprising HFKQYECSSPPNNQVIPCQP-TIIERNITEIVYLTNTTIEKEICPKLVEYRNWSKP (SEQ ID NO:22) and concatenations thereof), are useful for a stalk to display immobilized ligands:

Additional stalk sequences can be tested (for suitability for use in the methods of the invention) using the assay described in Example 1, infra, but substituting the new stalk sequence for the fractalkine domain of Example 1. Briefly, to identify new suitable stalk region sequence, sequences encoding potential display stalks are cloned into an expression vector [e.g., pcDNA3.1/ Myc-His(-)B (Invitrogen™ Corp, Carlsbad Calif.) or other suitable vector (e.g., pcDNA3.1/ Myc-His(-)A/C (Invitrogen™ Corp.) or a similar vector], for example as an EcoRI-linked PCR fragment to form a fusion protein having an ELC ligand domain at the amino terminus and a 6xHis sequence at the carboxy-terminus. That is, the stalk-encoding sequence is inserted upstream in an analogous position as was used for fractalkine domain of the ELC-stalkokine (i.e., between an ELC binding motif and a poly-histidine immobilization domain. The resulting plasmid is expressed in mammalian cells (e.g., 293 cells) and the tethered ligand protein expressed, e.g., as described in Example 1. The tethered ligand is then assayed for ability to mediate binding of cells expressing CCR10, as described infra. Variations of this assay will be apparent to those of skill in the art.

3.3 Immobilization Domain

In various embodiments, the fusion protein has an immobilization domain to facilitate immobilization of the protein to a solid substrate. Often, immobilization domain is a short

TABLE 3A

Human Fractalkine Mucin-Repeat Region

IGEVKPRTTPAAGGMDESVVLEPEATGESSSLEPTPSSQEAQRALGTSPELPTGVT
GSSGTRLPPTPKAQDGGPVGTELFRVPPVSTAATWQSSAPHQPGPSLWAEAKTS
EAPSTQDPSTQASTASSPAPEENAPSEGQRVWGQGQSPRPENSLEREEMGPVP
AHTDAFQDWGPGSMAHVSVVPVSSEGTPSREPVASGSWTPKAEEPIHATMDPQR
LGVLITPVP (SEQ ID NO:3)

TABLE 3B

Human Fractalkine Mucin-Repeat Sequence Residues 100–336

GGTFEKQIGEVKPRTTPAAGGMDESVVLEPEATGESSSLEPTPSSQEAQRALGTS
PELPTGVTGSSGTRLPPTPKAQDGGPVGTELFRVPPVSTAATWQSSAPHQPGPSL
WAEAKTSEAPSTQDPSTQASTASSPAPEENAPSEGQRVWGQGQSPRPENSLERE
EMGPVPAHTDAFQDWGPGSMAHVSVVPVSSEGTPSREPVASGSWTPKAEEPIHA
TMDPQRLGVLITPVPDAQA (SEQ ID NO: 4)

TABLE 4

Mucin Repeat Domains

| 1. | IGEVKPRTTP | (SEQ ID NO: 5) |
| 2. | GGMDESVVLEP | (SEQ ID NO: 6) |
| 3. | TGESSSLEPTP | (SEQ ID NO: 7) |
| 4. | LGTSPELPTG | (SEQ ID NO: 8) |
| 5. | TGSSGTRLPPTP | (SEQ ID NO: 9) |
| 6. | VGTELFRVPPVS | (SEQ ID NO: 10) |
| 7. | AATWQSSAPHQ | (SEQ ID NO: 11) |
| 8. | PGPSLWAEAKTS | (SEQ ID NO: 12) |
| 9. | EAPSTQDPST | (SEQ ID NO: 13) |
| 10. | QASTASSPAP | (SEQ ID NO: 14) |
| 11. | VWGQGQSPRP | (SEQ ID NO: 15) |
| 12. | SLEREEMGPVP | (SEQ ID NO: 16) |
| 13. | AHTDAFQDWG | (SEQ ID NO: 17) |
| 14. | PGSMAHVSVVP | (SEQ ID NO: 18) |
| 15. | EGTPSREPVA | (SEQ ID NO: 19) |
| 16. | SGSWTPKAEEP | (SEQ ID NO: 20) |
| 17. | QRLGVLITPVP | (SEQ ID NO: 21) |

In related embodiments, the stalk region of the tethered ligand has a sequence from a fractalkine of a non-human species such as mouse (see, Lloyd et al, 1997, *Nature* 387:611–617; Genbank Accession No. AF010586) and other mammals (e.g., porcine, bovine, ovine, rat, rabbit, and non-human primate mammals).

In a related embodiment, the stalk domain is derived from other mucin family members, such as MUC-type mucins. MUC-type mucins are a family of structurally related mol- (i.e., fewer than 10 residues) epitope tag (i.e., a sequence recognized by a antibody, typically a monoclonal antibody) such as polyhistidine (Bush et al, 1991, *J. Biol Chem* 266:13811–14), SEAP (Berger et al, 1988, *Gene* 66:1–10), or M1 and M2 flag (see, e.g, U.S. Pat. Nos. 5,011,912; 4,851,341; 4,703,004; 4,782,137). In some embodiments of the invention, the tethered ligand does not have a separate immobilization domain. Instead, the stalk domain is directly conjugated to the substrate, the stalk domain is immobilized via an anti-stalk (i.e., mucin) sequence antibody, or via some other immobilization m method.

3.4 Production of Tethered Ligands

As noted supra, methods form constructing and expressing fusion proteins are well known. Fusion proteins generally are described in Ausubel et al., supra, Kroll et al., 1993, *DNA Cell. Biol.* 12:441, and Imai et al., 1997, *Cell* 91:521–30.

The tethered ligand fusion proteins of the invention are typically made by (1) constructing a vector (e.g., plasmid, phage or phagemid) comprising a polynucleotide sequence encoding the desired polypeptide, (2) introducing the vector into an suitable expression system (e.g., a prokaryotic, insect, mammalian, or cell free expression system), (3) expressing the fusion protein and (4) optionally purifying the fusion protein.

(1) In one embodiment, expression of the tethered ligand fusion protein comprises inserting the coding sequence into an appropriate expression vector (i.e., a vector that contains the necessary elements for the transcription and translation of the inserted coding sequence required for the expression system employed, e.g., control elements including enhancers, promoters, transcription terminators, origins of replication, a suitable initiation codon (e.g., methionine), open reading frame, and translational regulatory signals (e.g., a ribosome binding site, a termination codon and a polyadenylation sequence. Depending on the vector system and host utilized, any number of suitable transcription and translation elements, including constitutive and inducible promoters, can be used.

The coding sequence of the tethered ligand fusion protein includes ligand, stalk and immobilization domains as described elsewhere herein. Polynucleotides encoding the amino acid sequence for each domain can be obtained in a variety of ways known in the art; typically the polynucleotides are obtained by PCR amplification of cloned plasmids, cDNA libraries, and cDNA generated by reverse transcription of RNA, using primers designed based on sequences determined by the practitioner or, more often, publicly available (e.g., through GenBank). Typically, the primers include linker regions (e.g., sequences including restriction sites) to facilitate cloning and manipulation in production of the fusion construct. The polynucleotides corresponding to the ligand, stalk and immobilization regions are joined in-frame to produce the fusion protein-encoding sequence.

The tethered ligand proteins of the invention may be expressed as secreted proteins or as nonsecreted proteins. Preferably, the fusion proteins are secreted. When the naturally occurring ligand includes a signal peptide (e.g., chemokine ligands) secretion is easily achieved by including the signal sequence encoding DNA in the fusion gene. Alternatively, and in the case of ligands not naturally secreted, a heterologous or artificial signal peptide is included in the fusion protein (see, e.g., Lui et al, 1993, *PNAS USA*, 90:8957–61).

(2) The tethered ligand fusion protein vectors may be introduced into a cell (e.g., bacterial, yeast, insect, and mammalian cells) by a variety of methods. The nucleic acid expression vectors (typically dsDNA) of the invention can be transferred into the chosen host cell by well-known methods such as calcium chloride transformation (for bacterial systems), electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, *Cell* 88:223), agent-enhanced uptake of DNA, and other methods known in the art. See Ausubel, supra.

(3) A variety of expression systems suitable for expression of tethered ligands are known in the art. Useful bacterial expression systems include *E. coli*, bacilli (such as *Bacillus subtilus*), other enterobacteriaceae (such as *Salmonella, Serratia*, and various Pseudomonas species) or other bacterial hosts (e.g., *Streptococcus cremoris, Streptococcus lactis, Streptococcus thermophilus, Leuconostoc citrovorum, Leuconostoc mesenteroides, Lactobacillus acidophilus, Lactobacillus lactis, Bifidobacterium bifidum, Bifidobacteriu breve,* and *Bifidobacterium longum*). The tethered ligand fusion protein expression constructs useful in prokaryotes include recombinant bacteriophage, plasmid or cosmid DNA expression vectors, or the like, and typically include promoter sequences. Illustrative promoters include inducible promoters, such as the lac promoter, the hybrid lacZ promoter of the Bluescript7 phagemid (Stratagene, La Jolla Calif.) or pSport1 (Gibco BRL); phage lambda promoter systems; a tryptophan (trp) promoter system; and ptrp-lac hybrids and the like. Bacterial expression constructs optionally include a ribosome binding site and transcription termination signal regulatory sequences. Illustrative examples of specific vectors useful for expression include, for example, pTrcHis2, (Invitrogen, San Diego Calif.), When tethered ligand fusion protein is expressed in yeast, a number of suitable vectors are available, including plasmid and yeast artificial chromosomes (YACS) vectors. The vectors typically include expression control sequences, such as constitutive or inducible promoters (e.g., such as alpha factor, alcohol oxidase, PGH, and 3-phosphoglycerate kinase or other glycolytic enzymes), and an origin of replication, termination sequences and the like, as desired. Suitable vectors for use in Pichia include PPICZ, His6/pPICZB, pPICZalpha, pPIC3.5K, pPIC9K, pA0815, pGAP2A, B & C, pGAP2alpha A, B, and C (Invitrogen, San Diego, Calif.) and numerous others known in the art or to be developed. In one embodiment, the vector His6/pPICZB (Invitrogen, San Diego, Calif.) is used to express a His6-tethered ligand fusion protein fusion protein in the yeast Pichia pastoris. An example of a vector useful in Saccharomyces is pYES2 (Invitrogen, San Diego, Calif.).

Another expression system provided by the invention for expression of tethered ligand fusion protein is an insect system. A preferred system uses a baculovirus polyhedrin promoter. In one such system, Autographa californica nuclear polyhedrosis virus (AcNPV) is used as a vector to express foreign genes in Spodoptera frugiperda cells or in Trichoplusia larvae. The sequence encoding the gene of interest may be cloned into a nonessential region of the virus, such as the polyhedrin gene, and placed under control of the polyhedrin promoter. Successful insertion of the sequence, e.g., encoding the tethered ligand fusion protein, will render the polyhedrin gene inactive and produce recombinant virus lacking coat protein. The recombinant viruses are then used to infect *S. frugiperda* cells or Trichoplusia larvae, in which the tethered ligand fusion protein sequence is then expressed (see, for general methods, Smith et al., 1983, *J. Virol.*, 46:584; Engelhard et al., 1994, *Proc. Natl. Acad. Sci.* 91:3224–7). Useful vectors for baculovirus expression include pBlueBacHis2 A, B & C, pBlueBac4.5, pMelBacB and numerous others known in the art or to be developed. Illustrative examples of tethered ligand fusion protein expression constructs useful in insect cells are provided in Example 6, infra.

The present invention also provides expression systems in mammals and mammalian cells. As noted supra, tethered ligand fusion protein polynucleotides may be expressed in mammalian cells (e.g., human cells) for production of significant quantities of tethered ligand fusion protein polypeptides are well known in the art and include those described infra §5.1.1

Optimum expression times are conveniently determined by analysis of the secreted protein by Western blot analysis (e.g., using a common epitope tag, e.g,. poly histidine) for detection.

(4) It is sometimes desirable to purify a secreted tethered ligand fusion protein from cell media, and generally necessary to purify nonsecreted proteins prior to use. Purification can be carried out using a variety of methods, including, for example, metal-chelate affinity chromatography of fusion proteins containing polyhistidine tracts (e.g. $His_6$), protein A domains or fragments (which allow purification on immobilized immunoglobulin), and the domain utilized in the FLAGS extension/affinity purification system (Immunex Corp, Seattle Wash.).

The fusion proteins may be stored under any suitable conditions (e.g., frozen) and may to preserve integrity, e.g., stored Several stalkokines were seen to be sensitive to long term storage and repeated freeze thaws. To avoid excessive degradation the protein solutions were aliquoted and frozen at −20° C. or −80° C. for long term storage. Addition of protease inhibitors to the supernatants containing the stalkokines reduced the level of degradation and enhanced quality.

3.4.1 Activity Assays

If desired, the fusion protein can be tested to confirm that it retains the biological activity of the isolated ligand. For example, in the case of a chemokine ligand, as described in the Examples, standard binding and chemotaxis assays may be carried out using the tethered ligands (e.g., prior to immobilization).

4. IMMOBILIZATION AND PREPARATION OF ARRAYS 4.1 Immobilization on Substrates

In some embodiments, the tethered ligands (e.g., stalkokines) of the invention are immobilized on a solid surface. The substrate to which tethered ligand is bound may be in any of a variety of forms, e.g., a microtiter dish, a test tube, a dipstick, a microcentrifuge tube, a bead, a spinnable disk, and the like. Suitable materials include glass, plastic (e.g., polyethylene, PVC, polypropylene, polystyrene, and the like), protein, paper, carbohydrate, and other solid supports. Other materials that may be employed include ceramics, metals, metalloids, semiconductive materials, cements and the like.

As noted supra, in some embodiments, the fusion proteins are organized as an array. The term "array," as used herein, refers to an ordered arrangement of immobilized fusion proteins, in which particular different fusion proteins (i.e., having different ligand domains) are located at different predetermined sites on the substrate. Because the location of particular fusion proteins on the array is known, binding of receptor-bearing cells to that location can be correlated with specific binding of the receptor or receptors displayed by the cell and the ligand (e.g., chemokine) domain of the fusion protein.

Immobilization of fusion proteins on beads (individually or in groups) is another particularly useful approach. In one embodiment, individual tethered ligand fusion proteins are immobilized on beads, allowed to bind to cells expressing cognate receptors, and the resulting complex is separated from unbound cells. In one embodiment, mixtures of distinguishable beads are used. Distinguishable beads are beads that can be separated from each other on the basis of a property such as size, magnetic property, color (e.g., using FACS) or affinity tag (e.g., a bead coated with protein A can be separated from a bead not coated with protein A by using IgG affinity methods). According to one embodiment, each distinguishable bead is associated with a species or particular combination of ligand fusion proteins. Cell binding to particular tethered ligand fusion proteins may be determined; similarly, the effect of test compounds (i.e., agonists and antagonists of binding) may be determined.

4.2 Substrates and Methods for Immobilization

Methods for immobilizing proteins are well known in the art, and include covalent and non-covalent methods. It will be appreciated that the choice of method will depend in part on the substrate and detection system selected.

4.2.1 Non-covalent Immobilization

One suitable immobilization method is antibody-mediated immobilization. According to this method, an antibody specific for the sequence of an "immobilization domain" of the tethered ligand is itself immobilized on the substrate (e.g., by adsorption). One advantage of this approach is that a single antibody may be adhered to the substrate and used for immobilization of a number of different tethered ligands (sharing the same immobilization domain). For example, an immobilization domain consisting of poly-histidine (Bush et al, 1991, *J. Biol Chem* 266:13811–14) can be bound by an anti-histidine monoclonal antibody (R&D Systems, Minneapolis, MN); an immobilization domain consisting of secreted alkaline phosphatase ("SEAP") (Berger et al, 1988, *Gene* 66:1–10) can be bound by anti-SEAP (Sigma Chemical Company, St. Louis, Mo.); an immobilization domain consisting of a FLAG epitope can be bound by anti-FLAG. Other ligand-antiligand immobilization methods are also suitable (e.g., an immobilization domain consisting of protein A sequences (Harlow and Lane, 1988, ANTIBODIES A LABORATORY MANUAL, Cold Spring Harbor Laboratory; Sigma Chemical Co., St. Louis, Mo.) can be bound by IgG; and an immobilization domain consisting of strepavidin can be bound by biotin (Harlow & Lane, supra; Sigma Chemical Co., St. Louis, Mo.).

When antibody-mediated immobilization methods are used, glass is an especially useful substrate (e.g., microscope quality glass slides). When arrays are desired, the glass substrates may be printed with a hydrophobic (e.g., Teflon) mask to form wells. Preprinted glass slides with 3, 10 and 21 wells per 14.5 $cm^2$ slide "working area" are available from, e.g., SPI Supplies, West Chester, PA; also see U.S. Pat. No. 4,011,350). In certain applications, a large format (12.4 cm×8.3 cm) glass slide printed in a 96 well format is used; this format facilitates the use of automated liquid handling equipment and utilization of 96 well format plate readers of various types (fluorescent, calorimetric, scintillation). However, higher densities may be used (e.g., more than 1 tethered ligand per $cm^2$). Often the tethered ligand array will include at least about 3, at least about 5, at least about 10, at least about 15, at least about 20 or more different ligands.

Typically, antibodies are bound to substrates (e.g., glass substrates) by adsorption. Suitable adsorption conditions are well known in the art and include incubation of 0.5–50 ug/ml (e.g., 10 ug/ml) mAb in buffer (e.g., PBS, or 50 to 300 mM Tris, MOPS, HEPES, PIPES, acetate buffers, pHs 6.5 to 8, at 4° C. to 37° C. and from 1 hr to more than 24 hours.

Antibody-mediated immobilization may provide certain advantages over other methods for immobilization, due to the flexibility of the antibody hinge region, allowing the ligand domain to adopt additional orientations.

Usually, the fusion protein is immobilized prior to contacting with receptor-expressing cells, however, in some embodiments, the immobilization follows the contacting step.

4.2.2 Covalent Immobilization

As noted supra, the tethered ligand may be covalently bound or noncovalently attached through nonspecific bonding. If covalent bonding between a the fusion protein and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

5. INTERROGATION OF STALKOKINES AND STALKOKINE ARRAYS

According to the methods of the invention, cells expressing receptors (e.g., chemokine receptors) are contacted with one or more tethered ligand fusion proteins (e.g., individual ligands or an array of different tethered ligands) under conditions in which binding between the ligand and cognate receptor (if present) occurs.

Typically, the binding conditions are physiological conditions under which receptor-ligand interactions occur or are expected to occur. Thus, in one embodiment, the cells are contacted with the tethered ligand in a buffered solution (e.g., PBS, TBS, etc).

Binding is typically allowed to proceed for between 0.5 and 10 h (typically between 0.5 and 3 h, e.g., 1.5 h) at 14° C. to 37° C. (e.g., room temperature), with or without gentle agitation. Preferred cell concentrations for binding range from 0.5–5×10$^6$/ml (e.g., 1–2×10$^6$/ml), but concentrations outside this range may be used (e.g., in the case of rare cells from a patient sample).

In some embodiments, the cells are pretreated prior to incubation with the array or individual tethered ligands. For example, cells may be decorated with fluorescently labeled antibodies (e.g., anti-CD3 cell marker) or labeled intracellularly with fluorescent dyes such as Calcein (Molecular Probes, Eugene, Oreg.), or labeled using radioisotopes. Such labeling facilitates quantitation of cell binding to tethered ligands (e.g., sites on an array) as well as characterization of the binding cells. For example, in an experiment analyzing chemokine receptors expressed on T lymphocytes, PBMCs may be isolated and T cells stained for with fluorescein labeled anti-CD4 and rhodamine labeled anti-CD8. Typically the cells are stained for 30 minutes, washed 3× in PBS, and resuspended at 1×10$^6$ cells per ml in PBS. The cells are then contacted with a tethered ligand array described herein, and allowed to bind at room temperature for 1 hour. The slide is then washed to remove unbound cells, and the adherent cells detected using a fluorescent plate reader. The fluorescein tag and the rhodamine tag are separately detected, with co-localization identifying T cells.

By analysis of the tethered chemokine to which each cell type is bound, and the ratio of the two signals, the cell type being localized at a particular tethered ligand may be determined (i.e., the cell may be characterized and the cells quantitated). It will be apparent that by staining a heterogeneous population of cells (e.g., from a patient with multiple sclerosis or rheumatoid arthritis) subpopulations of cells expressing particular receptors, or combinations of receptors, can be identified, e.g., for diagnostic purposes. Similarly, this protocol is useful in drug development (e.g., screening for compounds that alter the binding pattern of individual T cells to the tethered chemokines).

5.1 Interrogation with Recombinant Cells Expressing Receptors

In one embodiment, the methods of the invention are practiced using recombinant cells expressing receptors (i.e., cells transiently or stably transfected with expression vectors encoding the receptor protein of interest).

5.1.1 Cells Expression Recombinant Receptor Proteins

The recombinantly expressed receptor proteins used in the assay may be any of a variety of binding proteins, such as seven transmembrane spanning, G protein coupled receptor class (e.g., chemokine receptors), receptor tyrosine kinases (e.g., EGF receptor, insulin receptor, IGF-1 receptor, NGF receptor, PDGF receptor, M-CSF receptor, FGF receptor, VEGF receptor) and receptors for any ligand or ligand class listed in Table 2, supra. Exemplary receptors are shown in Table 1. Additional description of 7-transmembrane receptors, including links to sequence databases, is found at http://swift.embl-heidelberg.de/7tm/phylo/phylo.html. Numerous additional protein binding receptors are described in the literature and/or in GenBank. Using this information, one of ordinary skill cab prepare cells expressing a variety of receptors using routine techniques.

Transformed cell lines expressing receptors of interest and/or expression vectors encoding various receptors are known (see, e.g., American Type Culture Collection, 10801 University Boulevard Manassas, Va. 20110–2209; http://www.atcc.org/). Alternatively, provided with the DNA sequence of the gene or cDNA encoding a receptor, the receptor may be expressed using routine methods for expression of recombinant proteins. It will be understood that it usually is not necessary to express a full-length or naturally occurring receptor sequence; a portion, variant or fragment capable of binding the ligand is sufficient.

Usually, the receptor-encoding sequence of interest is cloned into a "recombinant expression cassette" expression vector and introduced (e.g., transfected) into an appropriate host cell.

Although receptors may be expressed in a variety of cell types capable of expressing a membrane-bound receptor protein (e.g., insect, and the like), the receptors used in the present invention typically are expressed in mammalian cells.

Host cells useful for receptor expression include, but are not limited to, insect cell systems infected with recombinant virus expression vectors (e.g., baculovirus), mammalian cells expression systems and the like. See, e.g., Ausubel et al., supra. In mammalian host cells, a number of expression systems may be utilized, e.g., constitutive expression vectors such as pCMV-myc (Clonetech, Palo Alto Calif.), inducible expression system such as pTRE2 (Clonetech, Palo Alto Calif.) (using tetracycline induction), vectors such as the bicistonic vector pIRES (Clonetech, Palo Alto Calif.) capable of driving the receptor and a drug resistance gene, and the like. In addition, a host cell strain may be chosen which modulates the expression of the inserted sequences, or modifies and processes the gene product in a specific fashion desired, e.g., modifications (e.g., glycosylation) and processing (e.g., cleavage) of protein products may be important for the function of the protein. To this end, eukaryotic host cells which possess the cellular machinery for proper processing of the primary transcript, glycosylation, and phosphorylation of the gene product may be used. Such host cells include, but are not limited to, monkey kidney CV1 line transformed by SV40 (COS-7, ATCC CRL 1651); human embryonic kidney line (293; Graham et al., *J. Gen. Virol.* 36:59 (1977)); baby hamster kidney cells (BHK, ATCC CCL 10); CHO (ATCC CCL 61 and CRL 9618); mouse sertoli cells (TM4, Mather, *Biol. Reprod.* 23:243–251 (1980)); monkey kidney cells (CV1 ATCC CCL 70); African green monkey kidney cells (VERO-76, ATCC CRL 1587); human cervical carcinoma cells (HeLa, ATCC CCL 2); canine kidney cells (MDCK, ATCC CCL 34); buffalo rat,liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather, et al., Annals N.Y. *Acad. Sci.* 383:44–46 (1982); MDCK cells (ATCC CCL 34 and CRL 6253); HEK 293 cells (ATCC CRL 1573); and WI-38 cells (ATCC CCL 75; ATCC: American Type Culture Collection, Rockville, Md.). The use of mammalian tissue cell culture to express polypeptides is discussed generally in Winnacker, FROM GENES TO CLONES (VCH Publishers, N.Y., N.Y., 1987).

For long-term, high-yield production of recombinant proteins, stable expression is preferred. For example, cell lines which stably express receptors may be engineered. Rather than using expression vectors which contain viral origins of replication, host cells can be transformed with the receptor encoding DNA controlled by appropriate expression control elements (e.g., promoter, enhancer, sequences, transcription terminators, polyadenylation sites, etc.), and a selectable marker. When appropriate, codon usage may be modified for expression in non-human cells or non-mammalian cells. Following the introduction of foreign DNA, engineered cells may be allowed to grow for 1–2 days in an enriched medium, and then switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the receptor proteins on the cell surface. A number of selection systems may be used, including but not limited to, the herpes simplex virus thymidine kinase (Wigler et al., 1977, *Cell* 11:223), hypoxanthine-guanine phosphoribosyltransferase (Szybalska & Szybalski, 1962, *Proc. Natl. Acad. Sci. USA* 48:2026), and adenine 5 phosphoribosyl transferase (Lowy et al., 1980, Cell 22:817) genes which can be employed in tk$^-$, hgprt$^-$or aprt$^-$cells, respectively. Also, antimetabolite resistance can be used as the basis of selection for dhfr, which confers resistance to methotrexate (Wigler et al., 1980, *Natl. Acad. Sci. USA* 77:3567; O'Hare et al., 1981, *Proc. Natl. Acad. Sci. USA* 78:1527); gpt, which confers resistance to mycophenolic acid (Mulligan & Berg, 1981), Proc. Natl. Acad. Sci. USA 78:2072); neo, which confers resistance to the aminoglycoside G418 (Colberre-Garapin et al., 1981, *J. Mol. Biol.* 150:1); and hygro, which confers resistance to hygromycin (Santerre et al., 1984, *Gene* 30:147). Additional selectable genes have been described, namely trpB, which allows cells to utilize indole in place of tryptophan; hisD, which allows cells to utilize histinol in place of histidine (Hartman & Mulligan, 1988, *Proc. Natl. Acad. Sci. USA* 85:8047); ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.) and glutamine synthetase (Bebbington et al., 1992, Biotech 10:169). Alternatively, homologous recombination into an advantageous site may be used to introduce DNA into cells (e.g., murine embryonic stem cells).

When interrogating a tethered ligand or tethered ligand array with a recombinant cell, it has been observed that better signal results when the cells are subcloned ("split") 1–2 days before the assay.

5.1.2 Characterization of Orphan Receptors

In one embodiment, the reagents and methods of the invention are useful for identifying ligands that bind to an orphan receptor. There are many putative receptors having various predicted biological functions that have no known ligands. According to the invention, cloned orphan receptors are recombinantly expressed, as described herein, and the binding of the orphan-receptor-expressing cell to a variety of tethered ligands is tested. Based on the profile of binding, a ligand or ligands can be assigned to the receptor.

Usually, one of skill is able to assign an orphan receptor to a specific class of receptors based on sequence homology or other characteristics. It will be recognized that, in such a case, the tethered ligand corresponding to the orphan receptor will usually, or initially, be interrogated with ligands known or believed to bind receptors of this class. For example, an orphan receptor with homology to a CXC chemokine receptor would initially be interrogated with ligands known to interact with CXC chemokine receptors. Similarly, an orphan receptor with homology to one or more classes of chemokine receptors will usually, or initially, be interrogated with chemokine ligands.

5.2 Interrogation with Populations of Cells

In various embodiments, the invention provides methods for analyzing the receptor (e.g., chemokine receptor) profile of a population of cells. The terms "receptor profile" or "profile of receptor expression" (used interchangeably) refer to the complement of cell-surface displayed receptors (i.e., membrane bound extracellular receptors) on a cell type (e.g., cell line or purified cell type) or in a heterogeneous population of cells (e.g., a cell sample from a patient), as detected in an assay. Thus, in an assay for a set of chemokine receptors, the term "receptor profile" for a cell line will refer to the set of those chemokine receptors displayed by cells of the cell line (without regard to other receptors, e.g., growth factor receptors, displayed). Similarly, the term "receptor profile" for a heterogeneous mixture of cells refers to the set receptors displayed by the cells of the population, even though not every cell may display the same set of receptors. As is discussed infra, the receptor profile of a cell population can also include information about the number and/or type of cells in the population binding each of several receptors.

Determining the receptor profile for populations of cells is useful in a variety of applications including diagnosis or prognosis of diseases in patients (or nonhuman animals, including medical models); profiling populations of individuals; assessment of the effect of a drug or treatment on a patient, and others.

5.2.1 Diagnosis and Prognosis

Different types of cells express different extracellular receptors. Moreover, the receptors expressed by any particular cell type may vary with the developmental stage of the cell, the cell environment, and location. For example, virally-infected cells may express different receptors than similar uninfected cells. Further, the presence or absence of cells expressing certain receptors (i.e., a cell population with a particular receptor profile) at a particular location is indicative of the state of health of an individual. Examples include the presence of leukocytes and other cells at sites of inflammation, and the presence of malignant cells in a sample.

Accordingly, the present invention provides diagnostic methods in which a population of cells is obtained from a patient suspected of suffering from a disease and the receptor profile for the population is determined using the assay methods described herein (i.e., contacting the cell population with one or more immobilized tethered ligand fusion proteins and identifying the ligands bound by the cells in the population). The receptor profile is then compared to a profile characteristic of the disease state and a profile characteristic of a healthy state, and a diagnosis is based on the comparison.

Examples of populations of cells include, without limitation, (1) cells from disease tissues and fluids, (2) cells from patient populations, (3) cells taken from patients at various times during the progression of disease or treatment. Thus, in one embodiment, cells are obtained from a tissue or fluid from an individual suffering from a disease, e.g., synovial fluid from an individual with rheumatoid arthritis; cerebral-spinal fluid from individuals with multiple sclerosis and Alzheimer's disease, bronchial alveolar lavage (BAL) fluid from patients with asthma, sarcoidosis, tuberculosis, adult respiratory distress syndrome and other inflammatory and infectious diseases, fetal cells, tissues, and biopsy (e.g., from tissues such as muscle, bone marrow, lymph node, liver, brain, and others). The reagents and methods of the invention are used to determine the population of receptors (e.g., chemokine receptors or "CKRs") expressed in the population and compared, for example, to the CKRs expressed in normal (e.g., non-disease) tissue. The normal and nondiseased tissue may be from the same subject, or from two or several different subjects. Differentially expressed CKRs define specific molecular disease targets for therapeutic intervention.

Cells may be obtained from patients suffering from any of a variety of diseases including without limitation diseases and conditions associated with inflammation, infection and cancer, e.g., (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), multiple sclerosis, systemic lupus erythematosus, diabetes, glomerulonephritis, and the like, (3) graft rejection (including allograft rejection and graft-vs-host disease), and (4) other diseases in which undesired inflammatory responses are to be inhibited (e.g., atherosclerosis, myositis); cancers, diseases in which angiogenesis or neovascularization play a role (neoplastic diseases, retinopathy and macular degeneration), infectious diseases and immunosuppressive diseases.

Further information about the population is obtained by quantitating and/or characterizing the cells bound to one or more of the ligands (e.g., by counting, sorting, immunostaining, and the like).

5.2.2 Drug Assessment

The reagents and methods of the invention are also useful for monitoring the effect of a drug or treatment on a patient. Cells from an individual or nonhuman animal are obtained from prior to and after treatment for a disease, or before or after onset or progression of a disease, before or after exposure to a pathogen, before and after immunization, and the like, and changes in the profile of receptor expression assayed by comparing the results. Further information about the populations is obtained by quantitating and/or characterizing the cells bound to one or more of the ligands (e.g., by counting, sorting, immunostaining, and the like). The drug assessment can be carried out repeatedly during a course of treatment.

5.2.3 Profiling Populations

In another related embodiment, the methods of the invention are used for "profiling" populations of individuals. In an exemplary embodiment, it is useful to determine the receptor profile (e.g., CKR profile) of cells (e.g., blood cells or leukocytes) from specific populations of individuals in order to group the individuals into cohorts of individuals expressing a particular receptor profile, or into cohorts of individuals expressing a particular receptor (e.g., on particular cells). For example, to plan a clinical trial for a CCR3 agonist to inhibit the binding of eotaxin to CCR3 expressed on eosinophils (e.g., for treatment to retard the activity of eosinophils in asthma), it will be useful to profile a large sample of individuals in the general population for the presence of CCR3. A subset of the population deficient in eosinophil binding to eotaxin-stalkokines can be identified and excluded from the clinical trial. Similarly, CCR3 expression can be correlated with other characteristics or markers (e.g., gender, age, or genetic or ethic variants).

5.3 Interrogation with Membrane Preparations

In addition to interrogating with recombinant or naturally occurring cells expressing the receptors of interest, a membrane preparation may be obtained from such cells and or cell homogenates may be used in the assays of the invention. Membrane preparations may be prepared using routine methods, e.g., hypotonic lysis and centrifugation (see, e.g., Dairaghi et al, 1999, *J. Biol. Chem.* 274:21569–74).

6. METHODS OF DETECTION

Cell binding to tethered ligands and arrays can be detected and quantitated in a number of ways. Cells can be observed (and counted) visually (i.e., using a microscopy) with or without prior staining. Alternatively, automated and semi-automated detection systems (e.,g., fluorometric imaging plate readers, scintillation counters, "96-well" plate readers) may be used to measure the signal associated with particular tethered ligands (e.g., sites on an array), particularly when the receptor bearing cells are labeled with a detectable label. As used herein, a "detectable label" has the ordinary meaning in the art and refers to an atom (e.g., radionuclide), molecule (e.g., fluorescein), or complex, that is or can be used to detect (e.g., due to a physical or chemical property), indicate the presence of a molecule or to enable binding of another molecule to which it is covalently bound or otherwise associated. Detectable labels suitable for use in the present invention include any composition detectable by spectroscopic, photochemical, biochemical, immunochemical, electrical, optical or chemical means. Labels useful in the present invention include biotin for staining with labeled streptavidin conjugate, magnetic beads (e.g., Dynabeads™), fluorescent dyes (e.g., fluorescein, Texas red, rhodamine, green fluorescent protein, enhanced green fluorescent protein, lissamine, phycoerythrin, Cy2, Cy3, Cy3.5, Cy5, Cy5.5, Cy7, FluorX [Amersham], SyBR Green I & II [Molecular Probes], and the like), radiolabels (e.g., $^3$H, $^{125}$I, $^{35}$s, $^{14}$C, or $^{32}$P), enzymes (e.g., hydrolases, particularly phosphatases such as alkaline phosphatase, esterases and glycosidases, or oxidoreductases, particularly peroxidases such as horseradish peroxidase, and others commonly used in ELISAs), substrates, cofactors, inhibitors, chemiluminescent groups, chromogenic agents, and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art.

In one embodiment, the association of receptor and tethered ligand is detected using the microswitch technology described at http://www.ece.neu.edu/edsnu/zavracky/mfl/programs/relay/relay.html.

If desired, cells may be fixed (e.g., using cross-linking agents such as glutaraldehyde) prior to detection.

As noted supra it will sometimes be convenient to stain receptor-bearing cells prior to or after contacting the cells with the tethered ligands according to the invention. In one illustrative embodiment, fluorescein isothiocyanate (FITC) labeled anti CD20 antibody is used to mark B cells, and rhodamine labeled anti CD3 is used to mark T cells. Visualization and quantitation under UV illumination and the correct wavelength filter sets would discern between the different cell types.

7. DATA ANALYSIS

Modes of analysis of the binding of receptor bearing cells to the tethered ligands and arrays of the invention will be apparent to one of skill following the guidance of this disclosure. Typically, analysis of the binding of the receptor expression cell line to the tethered array is done after quantitation of cell binding by enumeration, fluorescence, or scintillation. Usually, binding is done in triplicate and the average (mean) of the value is used for analysis.

Initially a baseline of non-specific binding is determined. The measurements for the wells in which a non-binding tethered ligand (e.g. a tethered chemokine of a subclass and does not bind a test chemokine receptor) serves as an appropriate baseline. Additional appropriate baselines can be determined by the binding measured for a non-ligand containing immobilized stalk (i.e., a "tethered ligand" lacking the ligand domain). Additionally, a mock-transfected control containing supernatant of a cell line that was processed through the transfection protocol but does not contain any plasmid capable of making the tethered ligand (such as the parental vector pcDNA3.1) may be used. A positive control also may be used in some embodiments (e.g., a tethered ligand known to bind to a particular receptor-bearing cell). Suitable positive controls exhibit binding at least about two-fold higher than base line, often about 10-fold higher than base line, and frequently at least about 100-fold higher than base line.

Authentic binding (e.g. binding occurring through the transfected receptor and the tethered ligand) can be verified by competition assays. In one embodiment, a soluble form of the ligand (i.e., corresponding to the ligand motif of the tethered ligand) or a soluble (non-immobilized) form of the tethered ligand is added in excess (e.g. 100 fold molar excess) to the cell line expressing the receptor for a pre-incubation period (e.g., 5 to 20 minutes, typically 15 minutes). The effect on binding is determined as described supra. Authentic binding is inhibited by the addition of soluble ligand. Occasionally, the binding can be mediated through endogenous receptors being expressed on the cell line being used. Use of the parental (i.e, non-recombinant) cell line as a control in a parallel analysis is used to detect this.

8. BINDING AGONISTS AND ANTAGONISTS

In various embodiments, the invention provides a method for identifying the ability of a test compound to modulate the interaction between a ligand and a receptor, between several ligands and a receptor, or between several ligands and several receptors.

In one embodiment, the binding assays of the invention, using either an array of tethered ligands or one or more individual tethered ligands is carried out in the presence and absence of a test compound. Decreased binding of receptor-bearing cells to the tethered ligand(s) in the presence of the test compound indicates that the test compound is acting as an antagonist of the interaction. Increased binding of receptor-bearing cells to the tethered ligand(s) in the presence of the test compound indicates that the test compound is acting as an agonist of the interaction. Because ligand receptor interactions have physiological effect (e.g., on cell metabolism), modulators of the interaction are expected to modulate that effect, and such modulators are often therapeutically useful, e.g., for producing pharmaceutical compositions.

The test compounds referred to supra may be any of a large variety of compounds, both naturally occurring and synthetic, organic and inorganic, and including polymers (e.g., oligopeptides, polypeptides, oligonucleotides, and polynucleotides), small molecules, antibodies, sugars, fatty acids, nucleotides and nucleotide analogs, analogs of naturally occurring structures (e.g., peptide mimetics, nucleic acid analogs, and the like), and numerous other compounds. Typically, test agents are added at a variety of concentrations, e.g., ranging from about 1 ng to about 1 g/ml, more often between 1 ug/ml and 1 mg/ml. Typically, test agents are added at a variety of molar concentrations, e.g. ranging from 1 picomolar to 1 molar, more often 1 nanomolar to 1 millimolar. Typically, test agents are added at a variety of concentrations, e.g. ranging from about 1 part per billion to about 1 part per hundred, more often from about 1 part per million to about 1 part per thousand.

In one embodiment, the "test compound" is a soluble form of the ligand moiety of the tethered ligand with which the receptor interacts. For example, the chemokines ELC, TECK and SLC have been demonstrated to inhibit (i.e., by competition) the binding of a CCR10-expressing cell to a tethered ligand having an ELC ligand domain (i.e., an ELC-stalkokine). See Example 1. More often, the "test compound" is an "synthetic test compound" usually a non-polypeptide compound, i.e., not having a sequence of a naturally occurring polypeptide.

In assessing the modulatory activity of a test agent, the test agent may be preincubated with the receptor bearing cell(s) prior to contacting of the cell(s) and the tethered ligand(s); added after the contacting of the cell(s) and the tethered ligand(s); added simultaneously with the contacting of the cell(s) and the tethered ligand(s). Test agents may also be administered to animals or in vitro or ex vivo cells or tissues to assay the effects of binding of populations of cells in a particular target tissue, or animal model.

In one embodiment of the invention, the effects of test agent(s) on the interaction between a particular tethered ligand and a specific receptor are tested. This approach is useful, for example, for validating an apparent interaction between a receptor (e.g., an orphan receptor) and a specific ligand and for high-throughput screening of agents that inhibit a specific receptor-ligand interaction (thereby modulating the biological function of the receptor or ligand). Methods for high-throughput screening are known (see, e.g., Williams, 2000, *Curr. Opin. Biotechnology* 11:42–46, and references cited therein).

In another embodiment, the arrays of the invention are used to assay the effect of test agents on the binding profile of a population of cells to a plurality of ligands.

9. KITS

In one aspect the invention provides kits (e.g., containers) containing (1) a tethered ligand array of the invention, or (2) one or several of the tethered ligand fusion proteins of the invention (e.g., a combination of at least 2, at least 5, or at least 10 different tethered ligands), e.g., in separate vials or (3) one, two or a plurality of the tethered ligand fusion proteins, with at least two of the tethered ligand fusion proteins immobilized different solid substrates (e.g., plates, slides, beads, or the like), e.g., different substrates (such as different beads).

10. EXAMPLES

The following examples are offered to illustrate, but not to limit, the claimed invention.

Example 1

This example demonstrates the use of the invention to determine the ligand specificity of an orphan receptor.

A. Abbreviations

ELC, EBl1 ligand chemokine; SLC, secondary lymphoid-tissue chemokine; TECK, thymus expressed chemokine; HEK293, human embryonic kidney 293 cells; PEI, polyethylenemine; CCR, CC chemokine receptor.

B. Materials and Methods

Human, viral and murine recombinant chemokines were obtained from R&D Systems (Minneapolis, Minn.; http://cytokine.rndsystems.com/cyt_cat/cyt_cat.html). $^{125}$I-labeled ELC and TECK were obtained from Amersham. Full length CCR10 expression constructs were made in pIRE-Spuro expression vector (Clontech, Palo Alto, Calif.) with a FLAG epitope tag and prolactin signal sequence, and used to generated stable transfectants in HEK293 cells. Transient and stable transfections for CCR10 and stalkokines were done using Superfect reagent (Qiagen, Valencia, Calif.) following manufacturer's protocol. Stably-transfected cells were generated by selection in 2 ug/mL puromycin for 7 days, and expression was confirmed by FACS analysis of the FLAG epitope using anti-FLAG M1 (Sigma, St. Louis, Mo.) and 2' anti-mouse PE conjugate (Coulter Immunotech, Miami, Fla.).

C. Stable Expression of CCR10 Protein.

The cloning and characterization of a new human chemokine receptor, designated "CCX CKR" or "CCR10" is described in Gosling et al., 2000, "Cutting edge: identification of a novel chemokine receptor that binds dendritic cell- and T cell-active chemokines including ELC, SLC, and TECK" *J Immunol.* 164:2851–6, incorporated herein by reference in its entirety for all purposes. The coding sequence of CCR10 is shown in FIG. 2

To assess the functional properties of the protein encoded by the CCR10 cDNA, including its potential chemokine binding profile, expression plasmids encoding CCR10 plus an added N-terminal Flag epitope were constructed. This allowed for detection and selection, using an anti-Flag mAb, of the most highly expressing stable transfectants. Human embryonic kidney 293 (HEK293) cells stably expressing the M1 flag epitope-tagged CCR10 were confirmed by FACS, and were selected for further analysis (HEK293-CCR10 cells).

D. Receptor Interrogation by Adhesion to Stalkokines.

To determine ligand binding to CCR10, HEK293-CCR10 cells were used to interrogate chemokine "stalkokines" (SK), i.e., molecules in which discrete chemokine domains were engineered to be tethered to the end of an extended stalk structure. Stalkokines were interrogated using 8-well chamber slides coated first with anti-His anchoring antibody (10 ug/ml in PBS overnight at RT), which were washed and 'blocked' (2% FBS/0.5% BSA in PBS); treated with 250 ul of HEK293 cell stalkokine supernatants (1 hr at 37C), and incubated with 500,000 HEK293-CCR10 transfectants (1.5 hrs at RT). Inhibition of adhesion by competition with soluble chemokines was done by incubating cells with 5–10 ug/ml of recombinant chemokines. In all cases, nonadherent cells were removed by washing in PBS; remaining adherent cells were fixed with 1% glutaraldehyde, photoimaged and counted. As a primary screen, this adhesion would reveal putative receptor-ligand interactions.

Figure 3A:
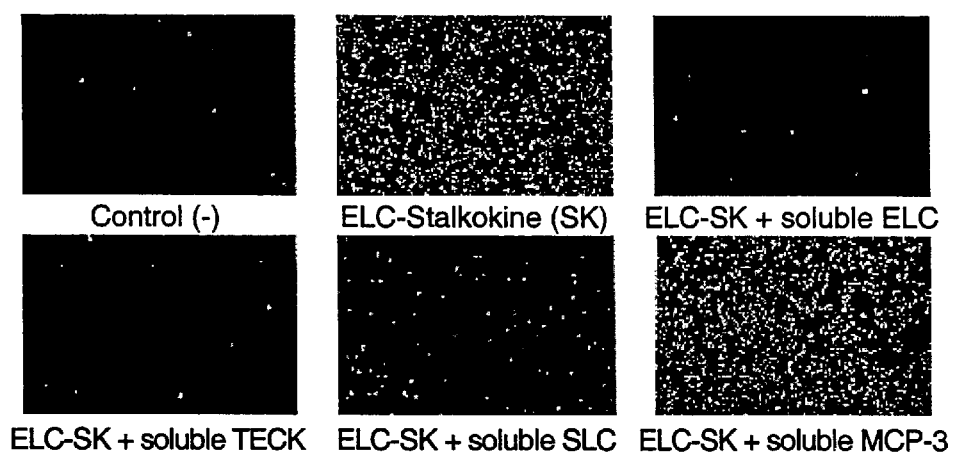
FIG. 3A shows interrogation of immobilized stalkokine (SK) by HEK293-CCR10 cells, where 'control' shows background adhesion of HEK293-CCR10 cells to wells containing no stalkokine (anchoring antibodies alone are present); "ELC-stalkokine (SK)" shows strong adhesion of HEK293-CCR10 cells to locations containing ELC-stalkokines immobilized via anchoring antibodies; "ELC-SK+soluble ELC", "soluble TECK", or "soluble SLC" shows ablation of adhesion in the presence of excess concentrations of soluble recombinant 'native form' chemokines as shown; "ELC-SK+soluble MCP-3" shows no diminution in adhesion in the presence MCP-3 as representative of many non-competing chemokines. Wild type HEK293 cells showed no adhesion to any of the sites (not shown).
Figure 3B:
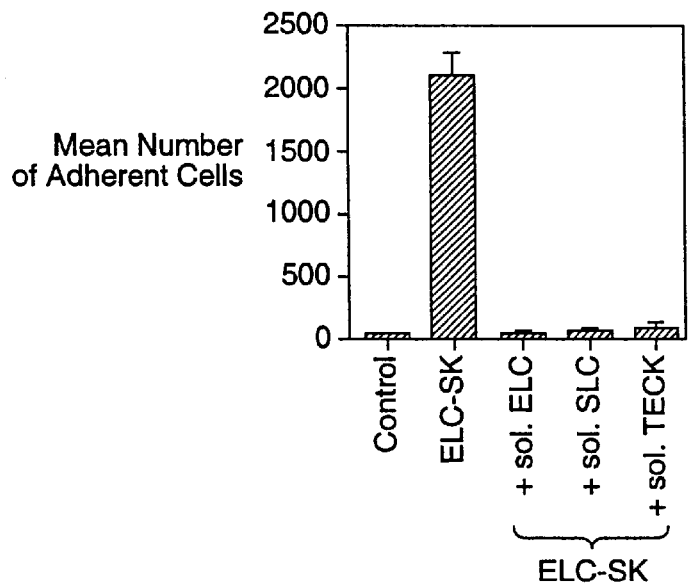
FIG. 3B shows the quantitation of adhesion of HEK293-CCR10 cells to ELC-stalkokine in the absence and presence of soluble chemokines from a representative experiment.
Figure 3C:
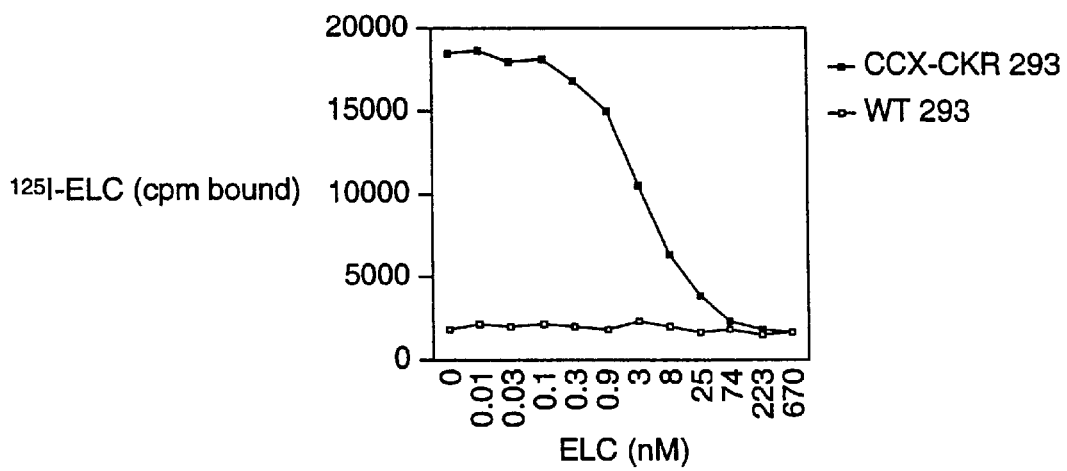
FIG. 3C shows the results of homologous competition binding assay using radiolabeled ELC in the presence of increasing concentrations of cold ELC on either HEK293-CCR10 cells (filled squares) or wild type HEK293 cells (open squares).

CCR10-expressing cells adhered very well to ELC stalkokines (ELC-SK; FIG. 3A). Furthermore ELC-SK mediated adhesion was abolished in the presence of soluble native ELC as a competitor (FIG. 3A, top row). A significant reduction in ELC-SK mediated adhesion of HEK293-CCR10 cells in the presence of soluble SLC, as well as soluble TECK, but not soluble MCP-3 (FIG. 3A, bottom row) was also observed. These experiments were performed and quantitated over several independent trials, an example of which is given in FIG. 3B, and were found to be highly reproducible. Moreover, radiolabeled ELC was used in a traditional homologous competition assay in the presence of increasing concentrations of unlabeled ELC. The results revealed significant binding of ELC to HEK293-CCR10 cells, but not to wildtype (wt) HEK293 cells (FIG. 3C). Nearly identical results were obtained in homologous competition of radiolabeled TECK with cold TECK (not shown). Taken together, the stalkokine-based adhesion and radiolabeled ligand binding/homologous competition assays indicate that CCR10 is a new chemokine receptor that bound a novel compliment of chemokines.

The spectrum of ligands that bind to CCR10 includes ELC, SLC, and TECK with high affinity, and BLC and vMIPII with lower affinity.

Example 2

This example describes the construction and expression of stalkokines, and the adhesion of receptor-expressing cells to immobilized stalkokines.

A. Preparation of Stalkokine Expression Plasmids

1. Amplification of CK Ligand Sequences

Chemokine ("CK") coding sequences were generated using the polymerase chain reaction (PCR) with oligonucleotides synthesized based on the published literature, as shown in Table 5. The amplified CK coding sequence was cloned into an expression vector encoding a human fractalkine stalk region coding sequence and a c-terminal epitope tag (poly-histidine). Starting material for the PCR reactions included previously cloned plasmids, cDNA libraries, and cDNA generated by reverse transcription of RNA, as indicated in the table.

Amplification was carried out using oligonucleotides containing unique restriction endonuclease sites (EcoR1 in most case, alternatively EcoRV or SmaI) for cloning purposes. The amplified chemokine fragments included the initiation methionine codon and leader peptide sequence, resulting in a secreted product.

For example, a polynucleotide encoding the entire MCP2 chemokine was generated by PCR amplification. The amplification oligonucleotides each included an EcoRI site. The PCR fragment contained the regions encoding the whole, unprocessed chemokine (leader sequence plus mature protein), including the codons for the initiating methionine, leader sequence, and entire chemokine coding sequence up to, but not including the stop codon (amino acid 1 (met) to 109 (pro) inclusive, Genbank accession number X99886).

Figure 4:
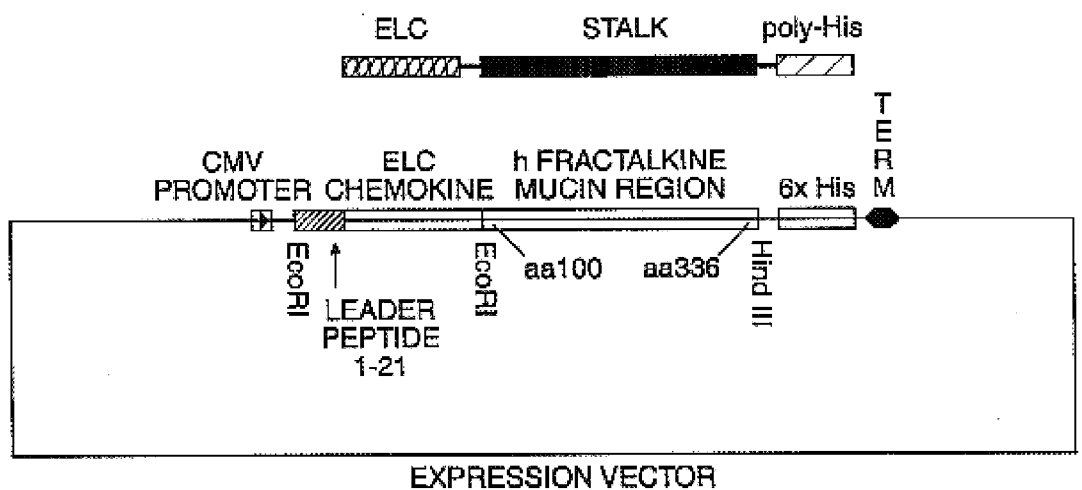
FIG. 4 shows a schematic diagram of an expression plasmid encoding an ELC-stalkokine. Not all details of the plasmid are shown (e.g., pA site, polylinker, Ori, selection markers are not shown).

Following amplification of the chemokine domain sequence, the DNA fragment was subcloned into the EcoRI (or EcoRV site) of the modified vector based on pcDNA3.1, encoding a human Fractalkine mucin stalk sequence (described below). See FIG. 4. The ligand motif is designed to be in frame by the construction of the oligonucleotides for the PCR synthesis of the fragment and the sequence of the construct is determined by DNA sequencing.

TABLE 5

| Chemokine | Forward Primer | Reverse Primer | Tissue Source |
|---|---|---|---|
| MDC GenBank accession number: U83171 | 5'-GGT GAA TTC ATG GCT CGC CTA CAG ACT GC (SEQ ID NO: 23) | 3'-GGT GAA TTC TTG GCT CAG CTT ATT GAG AAT CA (SEQ ID NO: 24) | RT-PCR from human immature dendritic cell RNA |
| HCC1 GenBank accession number: Z49270 | 5'-GGT GAA TTC ATG AAG ATC TCC GTG GCT GCC (SEQ ID NO: 25) | 3'-GGT GAA TTC GTT CTC CTT CAT GTC CTT GAT ATA G (SEQ ID NO: 26) | PCR from human placenta cDNA library |
| SLC GenBank accession number: AF001979, AB002409 | 5'-GGT GAA TTC ATG GCT CAG TCA CTG CT CTG (SEQ ID NO: 27) | 3'-GGT GAA TTC TGG CCC TTT AGG GGT CTG TG (SEQ ID NO: 28) | PCR from human EST clone |
| MIG GenBank Accession number NM 002416 | 5' GGT GAA TTC ATG AAG AAA A GT GGT GTT CTT TTC C (SEQ ID NO: 29) | 3'GGT GAA TTC TGT AGT CTT CTT TTG ACG AGA ACG (SEQ ID NO: 30) | reverse transcription of human fetal brain mRNA |
| IP10 GenBank Accession number NM 001565 | 5' GGT GAA TTC ATG AAT CAA ACT GCG ATT CTG A (SEQ ID NO: 31) | 3'GGT GAA TTC AGG AGA TCT TTT AGA CAT TTC CTT G (SEQ ID NO: 32) | human cDNA pool |
| H174/I-TAC GenBank accession number AF002985 | 5' GTG GAA TTC ATG AGT GTG AAG GGC ATG GC (SEQ ID NO: 33) | 3'GGT GAA TTC AAA ATT CTT TCT TTC AAC TTT TTT GA (SEQ ID NO: 34) | human placental cDNA library |
| Eotaxin1 GenBank accession number U46573 | 5' GGT GAA TTC ATG AAG GTC TCC GCA GCA CTT C (SEQ ID NO: 35) | 3' GGT GAA TTC TGG CTT TGG AGT TGG AGA TTT TTG (SEQ ID NO: 36) | human EST |
| TARC GenBank accession number NM 002987 | 5' GGT GAA TTC ATG GCC CCA CTG AAG ATG CT (SEQ ID NO: 37) | 3' GGT GAA TTC AGA CCT CTC AAG GCT TTG CAG (SEQ ID NO: 38) | reverse transcription of immature dendritic cell mRNA |
| MIP3alpha GenBank accession number U77035 | 5' GGT GAA TTC ATG TGC TGT ACC AAG AGT TTG C (SEQ ID NO: 39) | 3' GGT GAA TTC CAT GTT CTT GAC TTT TTT ACT GAG G (SEQ ID NO: 40) | human EST |
| ELC GenBank accession number U77180, NM 006274 | 5' GGT GAA TTC ATG GCC CTG CTA CTG GCC CT (SEQ ID NO: 41) | 3' GGT GAA TTC ACT GCT GCG GCG CTT CAT CT (SEQ ID NO: 42) | human EST |
| TECK GenBank accession number NM 005624 | 5' GGT GAA TTC ATG AAC CTG TGG CTC CTG GC (SEQ ID NO: 43) | 3' GGT GAA TTC CAG TCC TGA ATT AGC TGA TAT CAG (SEQ ID NO: 44) | human placental cDNA library |
| PARC GenBank accession number AB012113 | 5' GGT GAA TTC ATG AAG GGC CTT GCA GCT GC (SEQ ID NO: 45) | 3' GGT GAA TTC GGC ATT CAG CTT CAG GTC GC (SEQ ID NO: 46) | human placental cDNA library |
| SLC GenBank accession numberAF001979 | 5' GGT GAA TTC ATG GCT CAG TCA CTG CT CTG (SEQ ID NO: 47) | 3' GGT GAA TTC TGG CCC TTT AGG GGT CTG TG (SEQ ID NO: 48) | human EST |
| I309 GenBank accession numberAA931884 | 5' GGT GAA TTC ATG CAG ATC ATC ACC ACA GCC C (SEQ ID NO: 49) | 3' GGT GAA TTC TTT TCT TTT TGA CGG GCA GTG C (SEQ ID NO: 50) | human EST |
| MIP1alpha GenBank accession number AA031820 | 5' GGT GAA TTC ATG CAG GTC TCC ACT GCT GC (SEQ ID NO: 51) | 3' GGT GAA TTC GGC ACT CAG CTC TAG GTC GCT (SEQ ID NO: 52) | human cDNA pool |
| MCP4 GenBank accession number U59808 | 5' GGT GAA TTC ATG AAA GTC TCT GCA GTG CTT CTG (SEQ ID NO: 53) | 3' GGT GAA TTC AGT CTT CAG GGT GTG AGC TTT CC (SEQ ID NO: 54) | reverse transcription of human brain mRNA |
| MCP1 | 5' GGT GAA TTC ATG | 3' GGT GAA TTC AGT CTT | human EST |

TABLE 5-continued

| Chemokine | Forward Primer | Reverse Primer | Tissue Source |
|---|---|---|---|
| GenBank accession number AA024753 | AAA GTC TCT GCC GCC CTT (SEQ ID NO: 55) | CGG AGT TTG GGT TTG C (SEQ ID NO: 56) | |
| MCP2 GenBank accession number NM005623 | 5' GGT GAA TTC ATG AAG GTT TCT GCA GCG CT (SEQ ID NO: 57) | 3' GGT GAA TTC TGG CTT CAG ATT TTG AAA TAT TTG (SEQ ID NO: 58) | reverse transcription of immature dendritic cell mRNA |
| SDF1a GenBank accession number L36034 | 5' GGT GAATTC ATG AAC GCC AAG GTC GTG G (SEQ ID NO: 59) | 3' GGT GAA TTC CTT GTT TAA AGC TTT CTC CAG GT (SEQ ID NO: 60) | human EST |
| MCP5 | 5' GGT GAT ATC ATG AAG ATT TCC ACA CTT CTA TGC C (SEQ ID NO: 61) | 3' GGT GAT ATC GCC TAG ACA TGA AGG TTC AAG GAT G (SEQ ID NO: 62) | |
| HCC2 | 5' GGT GAA TTC ATG AAG GTC TCC GTG GCT GC (SEQ ID NO: 63) | 3' GGT GAA TTC TAT TGA GTA GGG CTT CAG CTT T (SEQ ID NO: 64) | |
| CLONE 391 | 5' GGT GAA TTC ATG AAG GTC TTC TCC TTG GTC ATG (SEQ ID NO: 65) | 3' GGT GAA TTC CGT TGA GGT GTT GCT CAG CTT C (SEQ ID NO: 66) | |
| BCA1 | 5' GGT GAT ATC ATG AAG TC ATC TCG ACA TCT CTG (SEQ ID NO: 67) | 3' GGT GAT ATC GGG AAT CTT TCT CTT AAA CAC TGG (SEQ ID NO: 68) | |
| PF4a | 5' GGT GAA TTC ATG AGC TCC GCAGCC GGG TTC (SEQ ID NO: 69) | 3' GGT GAA TTC ACT CTC CAA AAG TTT CTT AAT TAT TTT (SEQ ID NO: 70) | |
| PBP-like1 | 5' GGT GAA TTC ATG CCA CCC TGC AGC TGT G (SEQ ID NO: 71) | 3' GGT GAA TTC TAA AGC CAT TGT GAA TAT GAT CTG (SEQ ID NO: 72) | |
| EOTAXIN 2 | 5' GGT CCC GGG ATG GCA GGC CTG ATG ACC AT (SEQ ID NO: 73) | 3' GGT CCC GGG GCA GGT GGT TTG GTT GCC AG (SEQ ID NO: 74) | |
| MIP1beta | 5' GGT GAA TCC ATG AAG CTC TGC GTG ACT GTC C (SEQ ID NO: 75) | 3' GGT GAA TTC GTT CAG TTC CAG GTC ATA CAC GTA (SEQ ID NO: 76) | |
| MIP-3 | 5' GGT GAA TTC ATG AAG GTC TCC GTG GCT GC (SEQ ID NO: 77) | 3' GGT GAA TTC ATT CTT CCT GGT CTT GAT CCG T (SEQ ID NO: 78) | |
| MRP-1 | 5' GGT GAA TTC ATG AGA AAC TCC AAG ACT GCC A (SEQ ID NO: 79) | 3' GGT GAA TTC AGC AAT GAC CTT GTT CCC AGA T (SEQ ID NO: 80) | |
| Lymphotactin (LYNT) | 5' GGT GAA TTC ATG ATA CTT CTC ATC CTG GCC C (SEQ ID NO: 81) | 3' GGT GAA TTC GCC AGT CAG GGT CAC AGC TG (SEQ ID NO: 82) | |
| HCC4 | 5' GGT GAA TTC ATG AAG GTC TCC GAG GCT GC (SEQ ID NO: 83) | 3' GGT GAA TTC CTG GGA GTT GAG GAG CTG GG (SEQ ID NO: 84) | |
| MIP-1 gamma | 5' GGT GAA TTC ATG AAG CCT TTT CAT ACT GCC C (SEQ ID NO: 85) | 3' GGT GAA TTC TTG TTT GTA GGT CCG TGG TTG T (SEQ ID NO: 86) | |
| IL-8 | 5' GGT GAT ATC ATG ACT TCC AAG CTG GCC G (SEQ ID NO: 87) | 3' GGT GAT ATC TGA ATT CTC AGC CCT CTT CAA A (SEQ ID NO: 88) | |
| ENA-78 | 5' GGT GAA TTC ATG AGC TCC CTG TCC AGC CG (SEQ ID NO: 89) | 3' GGT GAA TTC GTT TTC CTT GTT TCC ACC GTC C (SEQ ID NO: 90) | |
| GROgamma | 5' GGT GAT ATC ATG GCC CAC GCC ACG CTC TC (SEQ ID NO: 91) | 3' GGT GAT ATC GTT GGT GCT CCC CTT GTT CAG (SEQ ID NO: 92) | |
| GRObeta | 5' GGT GAT ATC ATG GCC CGC GCC ACG CTC TC (SEQ ID NO: 93) | 3' GGT GAT ATC GTT GGA TTT GCC ATT TTT CAG C (SEQ ID NO: 94) | |
| NAP-2 | 5' GGT GAT ATC ATG AGC CTC AGA CTT GAT ACC ACC (SEQ ID NO: 95) | 3' GGT GAT ATC ATC AGC AGA TTC ATC ACC TGC C (SEQ ID NO: 96) | |
| GROalpha | 5' GGT GAT ATC ATG GCC CGC GCT GCT CTC TC (SEQ ID NO: 97) | 3' GGT GAT ATC GTT GGA TTT GTC ACT GTT CAG CAT C (SEQ ID NO: 98) | |
| vMIP | 5' GGT GAA TTC ATG GCC CCC GTC CAC GTT TT (SEQ ID NO: 99) | 3' GGT GAA TTC ATG GAC ACC AAG GGC ATC CT (SEQ ID NO: 100) | |

B. Stalk Expression Cassette

CK ligand coding sequences were cloned into the EcoR1 or EcoRV sites of the polylinker region of the expression vector pcDNA-FRAC. This vector includes a polylinker upstream of a human fractalkine stalk coding region fused to the myc epitope and poly-histidine coding region used for antibody tethering and subsequent purification. The coding region is under control of a CMV promoter.

pcDNA-FRAC was constructed by inserting a fractalkine mucin stalk coding sequence (corresponding to amino acids 100 to 336 (inclusive) of human fractalkine (Genebank Accession number U84487)) into the EcoRI and HindlII restrictions sites of vector pcDNA3.1(−)/Myc-His version B (Invitrogen) [hereinafter, "pcDNA3.1"]. The resulting vector (pcDNA3.1-FRAC) was used for expression of various chemokine ligands. This was accomplished by inserting a PCR-amplified ligand sequence into the vector upstream of, and in frame with, the stalk domain. The resulting vectors (and the encoded proteins) are generally referred to as "'chemokine'-FRAC", e.g., "MDC-FRAC", "TARC-FRAC" and the like.

A region of the multiple cloning site polylinker region from pcDNA3.1 is present in between the last amino acid of the chemokine ligand domain and the first amino acid (glycine) of the fractalkine mucin stalk region. Insertion of the PCR fragment encoding the chemokine into the polylinker puts the coding regions in frame, resulting in the proper full length translation of the fusion protein. The polylinker region encodes various amino acids, depending on the restriction sites used for the cloning of the chemokine domain. For example, if the EcoR1 Tinkered chemokine domain is cloned into the EcoR1 site of the pcDNA3.1-FRAC, the linker region will encode the additional amino acids glutamate-phenylalanine. As another example, if the EcoRV linkered chemokine domain is cloned into the EcoRV site, the linker region will encode the additional amino acids alanine-glutamate-phenylalanine. As yet another example, if the Smal linkered chemokine domain is cloned into the EcoRV domain (as a blunt end ligation), the linker region will encode the additional amino acids alanine-isoleucine-proline-alanine-glutamate-phenylalanine.

The final plasmid is prepared in bulk using standard protocols and the Qiagen purification system to generated pure plasmid in milligram amounts. Plasmid was stored in 10 mM Tris, 1 mM EDTA at 20° C.

C. Expression of Stalkokine in Cell Culture

The stalkokine synthesis is generated in in vitro cell culture using HEK293 (ATCC No. CRL-1573) or 293T (Pear et at, 1993, PNAS 80:8392–6) cell lines transiently transfected with the stalkokine expression plasmid. These cell lines were grown in DMEM supplemented with 10% FBS containing antibiotics, at a 60% confluence prior to transfection. On the day of transfection, the cells were transfected by the following protocol:

The cells were washed with PBS. 17 ug of plasmid DNA was resuspended in 825 ul of "Opti-MEM" reduced serum medium (Life Technologies, Rockville, Md.)). Superfect reagent (Qiagen) was added to the plasmid, mixed, and allowed to incubate at room temperature for 20 minutes. It is then added to the cells and incubated at 37° C., 5% $CO_2$ for 3 hours. Next, the cells are washed with PBS, and complete DMEM media containing 10% FBS and antibiotics are added. After overnight culture, the media was aspirated and replaced with DMEM with 2.5% FBS and antibiotics.

The supernatants were harvested from the transfected cells at 24, 48, 72. The transfected culture was supplemented with fresh media and incubated as above until the next harvest time. The supernatant was centrifuged to remove any cellular debris, and then transferred to a fresh tube. Several aliquots are made and the samples are stored at −20° C. until required. In some experiments, protease inhibitor cocktails were added to the clarified supernatant prior to storage.

Purification of the stalkokines was carried out using poly histidine affinity chromatography. Large scale transfections were done and the supernatants after culture were dialyzed to remove any very small molecule contaminants. The supernatant was passed over the nickel column twice, eluted with imidazole, and the eluate was dialyzed into PBS and analyzed. Usually significant purification was achieved with reasonable recoveries. This material was compared with the unpurified stalkokine by Western analysis, and total protein was determined. The material purified was typically 50–75% pure.

Purification is useful for a number of reasons: it removes contaminant molecules that could have a detrimental effect on stability of the stalkokine, allows easy comparison of equivalent amounts of material in assays, and facilitates quality control in preparing tethered ligand arrays.

D. Monitoring Expression by Western Blotting

The fusion protein is analyzed by Western blot analysis to confirm the expected length of the fusion protein and the presence of the poly histidine tail (which confirms the carboxy terminal is in the correct reading frame). In many cases, the amino-terminal chemokine domain is also interrogated by Western blot analysis looking with chemokine-specific antibodies which will only react with protein made in the correct frame.

Figure 5:
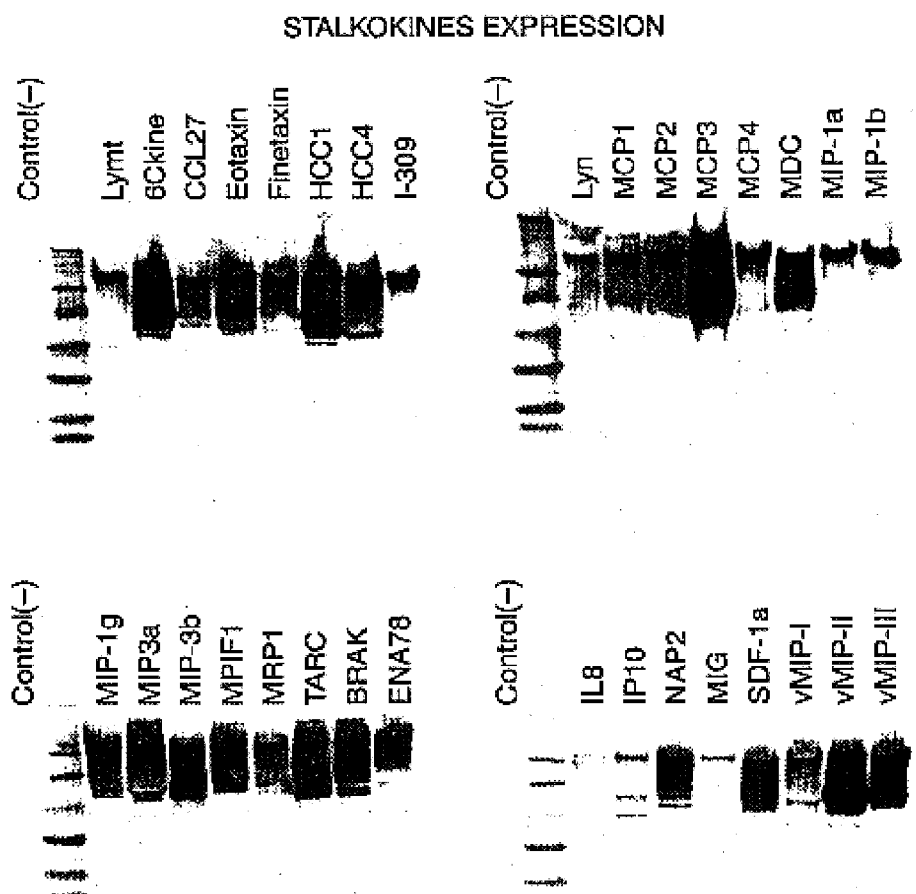
FIG. 5 shows Western blot analysis of 32 different stalkokines. Each individual stalkokine construct was transfected into 293T and supernatants containing the stalkokines were subjected to electrophoresis followed by Western blot analysis using the anti-poly histidine antibody. Equivalent volumes of supernatant were analyzed in each lane. Expression levels varied from a very robust accumulation in the case of MCP3 to a low level accumulation (IL-8). Enhanced stalkokine accumulation can be achieved by addition of protease inhibitors. Due to glycosylation, the apparent molecular weight of the soluble stalkokines increased from the typical 35 kDa to around 90 kDa. Partial glycosylation resulted in an intermediate molecular weight, and it demonstrated by the very broad band or smear of signal. MW markers =97.4, 68, 43, 29, 18.4, 14.3 kDa.

The success of the cell transfection was monitored using Western blotting procedures. Typically, 10 ul of supernatant was mixed with a denaturation solution containing reducing agents (DTT) and heated to 100° C. for 5 minutes. The protein sample was then loaded onto a 10–20% acrylamide Tricine gel and electrophoresed for 45 minutes at 100 V. The contents of the gel were transferred to a nitrocellulose membrane using standard transfer protocols. Transfer efficiency was determined by completeness of transfer of the prestained molecular weight markers. The membrane was blocked in a solution of Tris buffered saline, BSA and Tween-20. The membrane was then incubated for 1 hour with a primary antibody such as the anti-HIS antibody, or an antibody recognizing the chemokine domain. The primary antibody was washed off with three consecutive washes in TBS for 5 minutes with gentle agitation. The membrane was then incubated for 1 hour with the secondary antibody recognizing the Fc domain of the primary antibody. This secondary antibody has a covalently linked horseradish peroxidase enzyme attached for subsequent visualization. After washing off the secondary antibody, the membrane was visualized by incubation with a chromagenic substrate DAB until visible bands were generated, then stopped by washing in water. See FIG. 5.

E. Stalkokine Activity

The functional activity of the chemokine motif of an expressed stalkokine fusion protein was assessed by two methods: chemotaxis and displacement of labeled chemokines.

Figure 6:
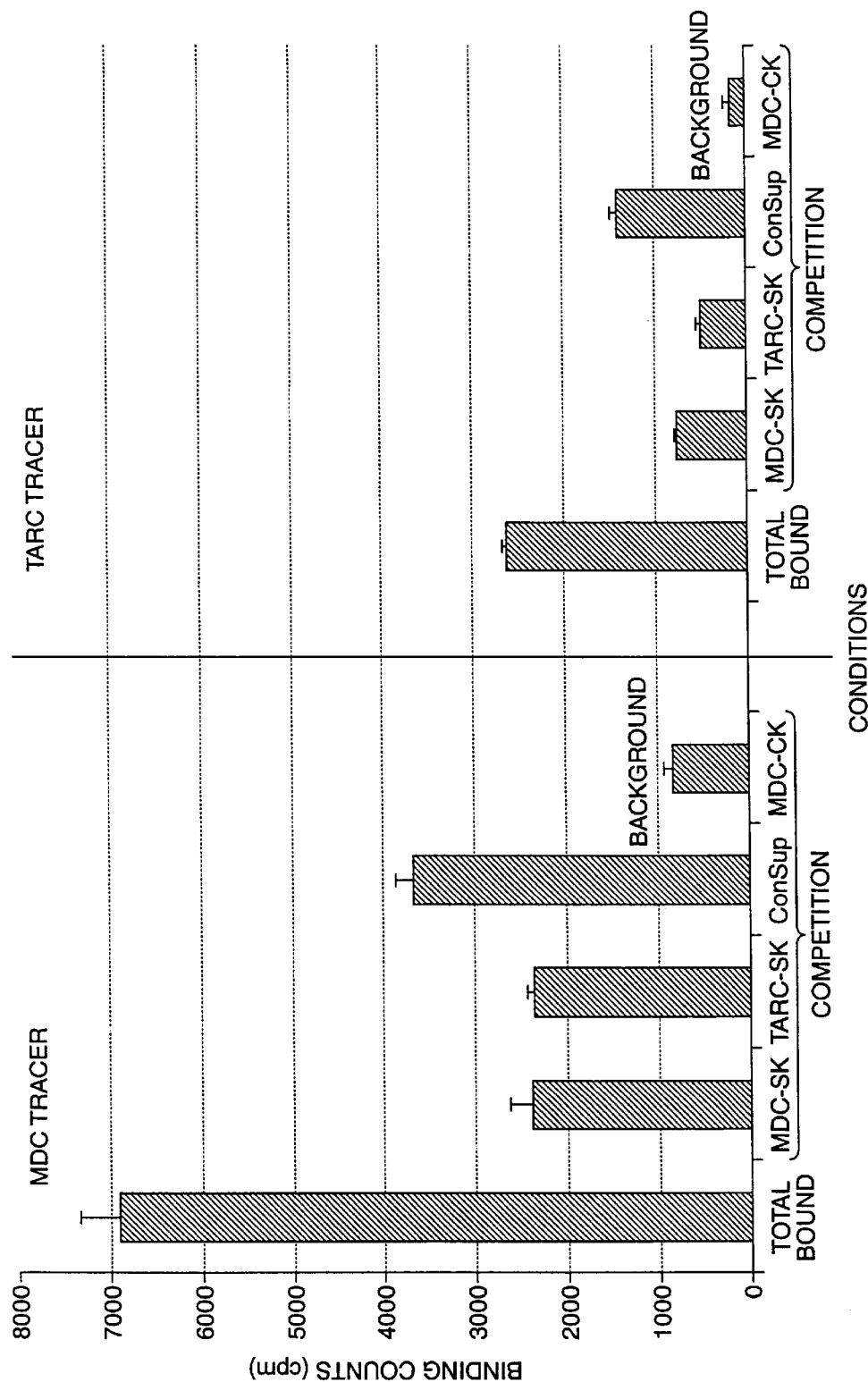
FIG. 6 shows a displacement assay showing competition by a stalkokine with binding of a radiolabeled tracer chemokine to its cognate receptor.

FIG. 6 shows a displacement assay showing competition by a stalkokine with binding of a radiolabeled tracer chemokine to its cognate receptor. CEM cells expressing CCR4 were used in a binding assay with radiolabeled MDC or TARC, as described in Dairaghi et al, 1999, *J. Biol. Chem.* 274:21569–74.

Briefly, CEM cells we added to radiolabeled chemokine "tracer" (MDC or TARC) in the presence of competitor molecules such as supernatants expressing the soluble MDC-FRAC (a stalkokine with a fractalkine stalk and an MDC ligand domain) or TARC-FRAC (a stalkokine with a fractalkine stalk and an TARC ligand domain). The cells and tracer were incubated and harvested by filtration, capturing the bound tracer. The material was then counted. "Total" is the amount of tracer bound with no competition. "MDC-SK" is the amount of binding in the presence of soluble MDC-FRAC fusion protein, "TARC-SK" is the amount of binding in the presence of soluble TARC-FRAC fusion protein, "ConSup" refers to competition with the control supernatant (conditioned media from CEN cells not expressing any strakokine), "MDC—CK" is the competition with soluble MDC chemokine, and demonstrated the background binding.

As is evident, there is considerable inhibition of binding of either MDC or TARC tracer to the CEM cells in the presence of the experimental supernatants. Part of this inhibition is due to other elements present in the control sup, but there is a significant further decrease specific to the recombinant MDC-FRAC or TARC-FRAC. The MDC—CK inhibition demonstrates the background binding and the maximal level of competition that one can achieve.

Chemotaxis assays were done on cell types known to possess the receptor for the chemokine ligand (Bacon et al, 1988, *Br J Pharmacol* 95:966–74).

Figure 7:
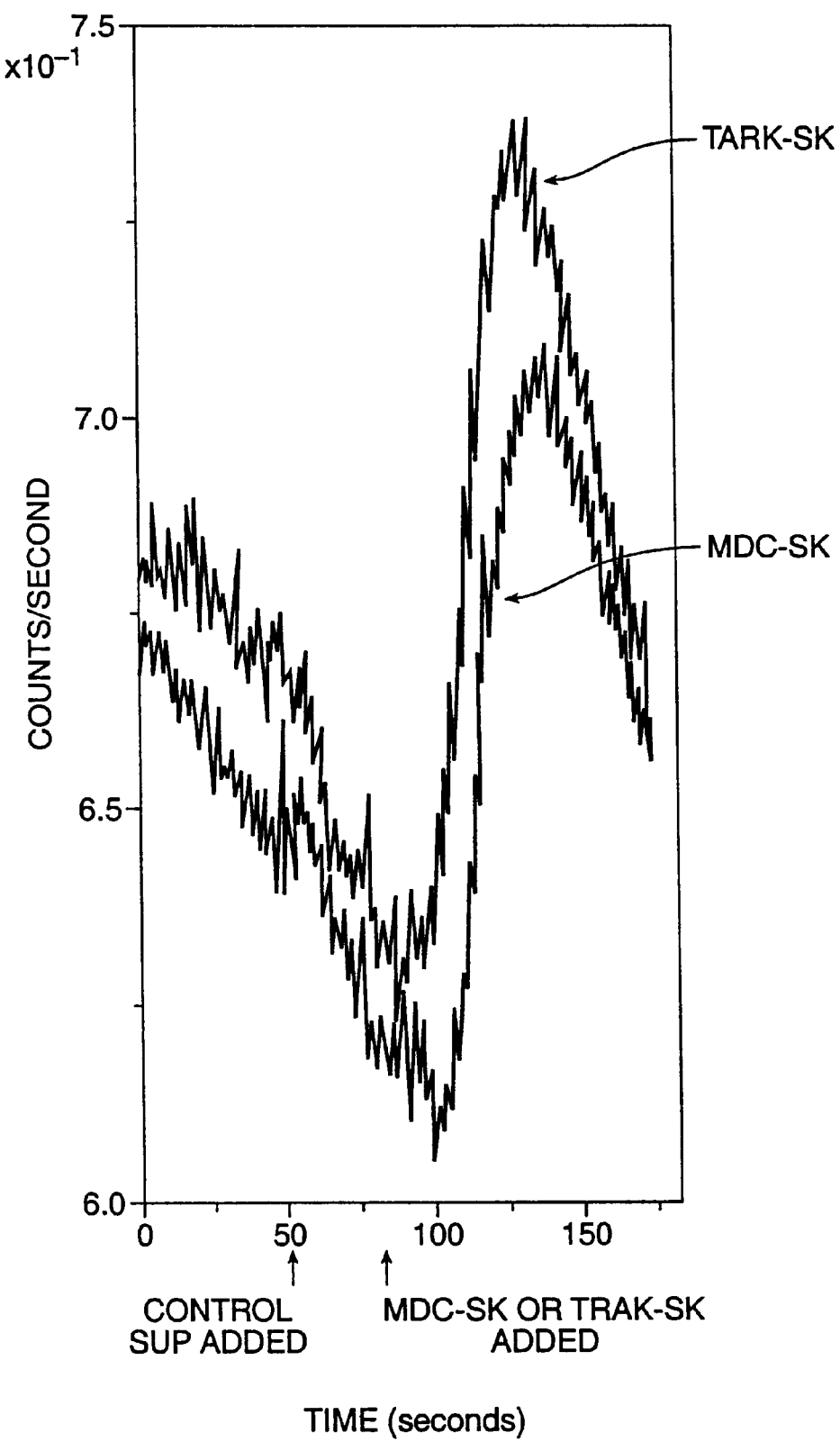
FIG. 7 shows a calcium mobilization assay using CEM cells expressing CCR4 receptors contacted with TARC-Stalkokine or MDC-Stalkokine, showing induction of calcium signaling in a receptor dependent manner.

FIG. 7 shows an assay in which CEM cells were "loaded" with INDO-1AM (Molecular Probes, Eugene, Oreg.) and subjected to calcium flux analysis as described in Dairaghi et al, 1997, *J. Biol. Chem.* 272:28206–209.

Briefly, CEM cells that express CCR4 were placed in a fluorimeter and monitored over time for changes in fluorescence. Two natural ligands for CCR4 are MDC and TARC. TARC-Fractalkine or MDC-Fractalkine (fusion protein supernatants), or control supernatants, were added at the following times: experiment 1, control supernatant added at 50 sec, TARK-FRAC at 80 sec; experiment 2, control supernatant at 50 sec and MDC-FRAC at 80 sec. The control supernatant did not result in any calcium influx, where as the TARC-FRAC or MDC-FRAC resulted in modest influx. This experiment demonstrates that the chemokine ligand fusion proteins are capable of causing signaling.

F. Adhesion of Stalkokine to Solid Surfaces

Stalkokines were immobilized on glass and polystyrene surfaces by binding to anti-histidine mAbs. The glass substrates were in the form of slides, either 8 well chamber slides, or glass slides printed with hydrophobic Teflon mask to generate wells. Standard microscope slides sizes had between 8 and 30 wells per slide.

In one set of experiments, five 8 well chamber slides (Lab-Tek II, Nalge Nunc International, Rochester, N.Y.), 250 ul of 10 ug/ml anti-his antibody (R&D Systems, Minneapolis, Minn.) in PBS was added to each well and incubated at room temperature overnight (typically 16 hours). Following, the liquid in each well was aspirated and washed once for approximately 5 minutes with 500 ul of PBS. The wells were then "blocked" (blocked for any additional protein binding sites) with the addition of 250 ul of blocking solution (2% fetal bovine serum, 0.5% BSA in PBS) and incubation for 1 hour at room temp (e.g., 20° C.). The liquid in each well was aspirated and 250 ul of supernatant containing the chemokine-stalk-immobilization domain fusion proteins (SDF1a-FRAC, finetaxin-FRAC, CCL27-FRAC, 1309-FRAC, MIP3a-FRAC, ELC-FRAC, SLC-FRAC, MDC-FRAC, TARC-FRAC, or BRAK-FRAC) or the control supernatant was added to two wells. Each slide contained two wells with control supernatant (from mock-transfected cells) and two wells with the positive control SDF1a (which binds the ubiquitous chemokine receptor CXCR4). The four other wells were for experimental samples. The supernatants were incubated for one hour at room temperature (typically 20° C.), then incubated for an additional hour at 37° C. The supernatants were aspirated off, and each well was washed once for 5 minutes with 500 ul of PBS. The slide was then ready for addition of cells for assay.

In a second set of experiments using two 96 well large format glass slides, 50 ul of 10 ug/ml anti-his antibody (R&D Systems, Minneapolis, Minn.) in PBS was added to each well and incubated at room temperature overnight (typically 16 hours) in a humidified chamber. Following, the liquid in each well was aspirated and washed once for approximately 5 minutes with 50 ul of PBS. The wells were then "blocked" (blocked for any additional protein binding sites) with the addition of 50 ul of blocking solution (2% fetal bovine serum, 0.5% BSA in PBS) and incubation for 1 hour at room temp (20° C.) in a humidified chamber. The liquid in each well was aspirated and 50 ul of supernatant containing one of the 32 chemokine-stalk-immobilization domain fusion proteins shown in FIG. 5 was added to 3 wells. Each slide contained 3 wells with the control supernatant (from mock-transfected cells) and 3 wells with the positive control SDF1a (which binds the ubiquitous chemokine receptor CXCR4). The other wells were for experimental samples. The supernatants were incubated for one hour at room temperature (typically 20° C.) in a humidified chamber, then incubated for an additional hour at 37C again in a humidified chamber. The supernatants were aspirated off, and each well was washed once for 5 minutes with 50 ul of PBS. The slide was then ready for addition of cells for assay.

G. Expression of Chemokine Receptors in Cell Culture

Several types of cells were used in binding experiments to stalkokines of the invention, including transfected mouse myeloma NSO cells containing a mammalian expression vector driving expression of the receptor of interest, e.g., CCR1, CCR4, CCR6, CCR7, CCR8, CXCR4, CMV US28 (gift of R&D Systems (Minneapolis, Minn.)). The results of this experiment are summarized in Table 6.

TABLE 6

| Cell types | Some Known Ligands | Binding to Stalkokine form |
|---|---|---|
| CCR1-NSO | Ckb8-1, MCP3 | no, yes |
| CCR4-NSO | MDC, TARC | yes, yes |
| CCR6-NSO | MIP3a | yes |
| CCR7-NSO | ELC, SLC | yes, no |
| CCR8-NSO | I309, vMIP1 | yes, yes |
| CCR10-NSO | ELC | yes |
| CXCR4-NSO | FK, vMIPII | yes |

*Negative controls (non-binding stalkokines) were done in every case
Ckb8-1 (also MPIF1), ELC (same as MIP3beta), SLC (same as 6Ckine).
FK = fractalkine H. Contacting Receptor-Expressing Cells and Stalkokine Arrays In an experiment, CCR1-NSO cells were grown, harvested, and resuspended in PBS at a 2×10$^6$ cells/ml. 250 ul of this cell suspension was added to each well of a 8 well chamber slide, with two wells coated with each of CKb8-1 FRAC, MCP3-FRAC, SDF1a-FRAC (positive control), or mock transfected supernatant (negative control) as previously described. The slides were incubated for 1.5 h at room temp, then the supernatant gently aspirated. The chamber portion of the slide was removed (using the apparatus provided by the supplier) and the slide was washed by gentle immersion into a petri dish containing PBS to a depth of 1 cm. This was repeated 3 times in total, and the slide was immersed in a 1% glutaraldehyde solution (in PBS) for 5 minutes at room temp. The cells were inspected and enumerated visually by microscopy. The cells bound to MCP3 but not CKb8 tethered ligands.

I. Displacement and Competition Analysis

In an experiment, CCR4-NSO cells were used to test binding competition. Harvested CCR4 NSO cells were resuspended at $2 \times 10^6$ cells per ml in PBS. 500 ul aliquots of cells were transferred into eppendorf tubes, and 5 ug of recombinant human chemokine (MDC or TARC, R&D Systems, Minneapolis, Minn.) was added (final concentration was 10 ug/ml), mixed briefly, and incubated at room temperature for 10 minutes. Following, 250 ul of the cells were added to each two wells of an 8 well chamber slide that had been precoated with the MDC-FRAC or TARC-FRAC as previously described. 250 ul of cells that were not pre-treated with soluble chemokine were added to additional wells. The slides were incubated for 1.5 hours at room temp, then the supernatant gently aspirated. The chamber portion of the slide was removed (using the apparatus provided by the supplier) and the slide was washed by gentle immersion into a petri dish containing PBS to a depth of 1cm. This was repeated 3 times in total, and the slide was immersed in a 1% glutaraldehyde solution (in PBS) for 5 minutes at room temperature. The cells were inspected and enumerated visually by microscopy. The cells bound to both the MDC-FRAC and TARC-FRAC, as expected. Competition with either soluble MDC or TARC reduced binding to background levels in both cases, as expected.

In another experiment, small molecule chemical compounds were tested on the binding of vMIPII-FRAC and US28-NSO. Three small organic compounds previously identified as inhibitors of binding between chemokine receptor US28 and VMIPII, were also observed to compete and inhibit binding between vMIPII-FRAC and US28-expressing NSO cells using the present invention.

Example 3

This example describes the binding of a chemokine receptor to an array of stalkokines, to determine the binding specificity of the receptor.

To interrogate the binding of CCR10 to a panel of chemokine elements, an array of tethered ligands is prepared. pc-FRAC-based stalkokines are prepared using at least about 3, at least about 5, at least about 10, at least about 15, at least about 20 or all of the ligand domains listed in Table 5. An array of stalkokines is prepared on a pair of 96 well slides precoated with the anti-polyhistidine antibody overnight and blocked for 1 hour as described supra. Each stalkokine is placed on three wells in a 30 ul volume per well and incubated for 1.5 hours in a humidified chamber at 37° C. Also included are negative controls, in triplicate, which include (1) a mock transfected supernatant, (2) an immobilized stalk region (with no chemokine domain), and (3) PBS. A SDF1a stalkokine (which binds CXCR4, a ubiquitously expressed chemokine receptor) is used as a positive control. Each set of positive and negative controls is included on each plate.

The supernatants are aspirated and the wells are washed twice with PBS. The CCR10 cell line is prepared during incubation with the stalkokine. The cell line is trypsinized from the culture flasks, and washed twice with PBS. The cells are resuspended at a concentration of 1 million cells per ml of PBS, 30 ul of the cell suspension are added to each well of plate, and incubated at room temperature without agitation for 1.5 hours at room temperature. The droplets are partially aspirated off (leaving approximately 5 ul, taking care not to disturb the cells resting on the surface) and placed slowly into a tray with PBS (approximately 150 mls, depth of 1 cm). Each of the four edges of the 96 well plate is lifted slowly to the surface of the liquid in each of three consecutive wells. The bound cells are stained with SybrGreen 1 (Molecular Probes, Eugene, Oreg.) for 30 min at a stain diluted 1 to 5000 in PBS. The 96 well plate is removed, drained of excessive liquid, and counted in a Packard Fluorescent plate reader with 480 nm excitation, 530 nm emission filter sets. The results are transferred to an Excel file for further analysis.

All references cited herein are incorporated herein by reference in their entirety and for all purposes to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for identifying an interaction between an orphan receptor and a ligand, said method comprising:
   (a) contacting a cell expressing the orphan receptor or a ligand-binding portion thereof with an array of different tethered ligand fusion proteins immobilized to a substrate, wherein
       each tethered ligand fusion protein comprises a ligand domain and a stalk domain,
       different tethered ligand fusion proteins have different ligand domains and are located at different locations on the substrate;
   (b) detecting binding of said cell at a location on the array; and
   (c) identifying the ligand for the orphan receptor from the identity of the ligand domain of the fusion protein at the binding location, wherein the ligand comprises the ligand domain of the fusion protein at the binding location.

2. The method of claim 1 wherein the cell expresses a recombinant receptor.

3. The method of claim 1 wherein the cell expresses a seven-transmembrane receptor.

4. The method of claim 3 wherein the cell expresses a chemokine receptor or a cytokine receptor.

5. The method of claim 1 wherein binding of the cell at a plurality of locations on the array is detected, whereby a plurality of ligands for the receptor are identified.

6. A method for identifying a modulator of an interaction between a receptor and a ligand, comprising:
   (a) contacting cells expressing the receptor or a ligand-binding portion thereof with an immobilized tethered ligand fusion protein in the absence of a test compound, and measuring binding of the cells to the tethered ligand fusion protein;
   (b) contacting cells expressing the receptor or a ligand-binding portion thereof with the immobilized tethered ligand fusion protein in the presence of the test compound, and measuring binding of the cells to the tethered ligand fusion protein, wherein
       the tethered ligand fusion protein in (a) and (b) comprises a ligand domain and a stalk domain and is immobilized to a substrate;
       the test compound is other than a known ligand for the receptor; and
   (c) comparing the level of binding in (a) and (b), wherein decreased binding of cells in the presence of the test compound indicates that the test compound is an inhibitor of the interaction between the receptor and the ligand comprising the ligand domain of said tethered ligand fusion protein, and wherein increased binding of cells in the presence of the test compound indicates that the test compound is an enhancer of the interaction between the receptor and the ligand comprising the ligand domain of said tethered ligand fusion protein.

7. The method of claim 6 wherein the tethered ligand fusion protein is one of an array of different tethered ligand fusion proteins immobilized to the substrate, different tethered ligand fusion proteins having different ligand domains and immobilized to different locations on the substrate.

8. The method of claim 6 wherein the receptor is a chemokine receptor.

9. A method for evaluating a cell according to its receptor profile, the method comprising:
   (a) contacting said cell with an array of different tethered ligand fusion proteins immobilized to a substrate, wherein
       each tethered ligand fusion protein comprises a ligand domain and a stalk domain; and
       different tethered ligand fusion proteins have different ligand domains and are located at different locations on the substrate;
   (b) determining whether said cell binds at one or more locations of the array; and
   (c) deciding, for each binding location, that the cell expresses a receptor that binds a ligand comprising the ligand domain of the tethered ligand fusion protein at that binding location.

10. The method of claim 9 comprising detecting binding of said cell at a plurality of locations of the array to determine the identity of a plurality of receptors expressed by the cell.

11. The method of claim 9 wherein
    the cell is one of a population of heterogeneous cells; and
    determining comprises determining whether different cells in the heterogeneous population bind at one or more locations of the array.

12. The method of claim 11 wherein the population is obtained from synovial fluid, cerebral-spinal fluid, bronchial alveolar lavage (BAL) fluid, or blood.

13. The method of claim 9 further comprising quantitating the level of cell binding at each location in the array.

14. The method of claim 9 further comprising characterizing the cells bound at different locations of the array, wherein characterizing comprises counting the cells at different locations, sorting the cells at different locations and/or immunostaining the cells at different locations.

15. A method for diagnosis, comprising:
    (a) obtaining a population of cells from a patient suspected of having a disease;
    (b) determining a receptor profile for the population comprising
        (i) contacting said population of cells with an array of different tethered ligand fusion proteins immobilized to a substrate, wherein
            each tethered ligand fusion protein comprises a ligand domain and a stalk domain;
            different tethered ligand fusion proteins have different ligand domains and are located at different locations on the substrate; and
        (ii) detecting binding of cells to one or more locations of the array, thereby identifying a receptor profile;
    (c) comparing said receptor profile with a receptor profile characteristic of the disease to determine if the patient has the disease.

16. The method of claim 15, wherein determining a receptor profile further comprises characterizing the cells bound at different locations of the array, wherein characterizing comprises counting the cells at different locations, sorting the cells at different locations and/or immunostaining cells at different locations.

17. The method of claim 16 wherein characterizing comprises immunostaining cells at different locations.

18. The method of claim 15 further comprising quantitating the binding of cells at different locations of the array.

19. The method of claim 15 wherein the disease is an inflammatory or allergic disease, or an autoimmune disease.

20. The method of claim 15 wherein the population is obtained from synovial fluid, cerebral-spinal fluid, bronchial alveolar lavage (BAL) fluid, or blood.

21. A method for detecting an effect of a drug or treatment on a patient comprising:
    (a) determining a first receptor profile for a first population of cells expressing one or more receptors from the patient, comprising (i) contacting cells with an array of different tethered ligand fusion proteins immobilized to a substrate, wherein each tethered ligand fusion protein comprises a ligand domain and a stalk domain, different tethered ligands having different ligand domains and located at different locations on the substrate; and (ii) detecting binding of cells to one or more locations of the array, thereby determining the receptor profile;

(b) administering the drug or treatment to the patient;

(c) determining a second receptor profile of a second population of cells from the patient by performing steps (i) and (ii) with the second population; and (d) comparing the first and second receptor profiles from (a) and (c) to determine the effect of the drug or treatment, if any, on receptor-expressing cells from the patient.

22. The method of claim 21 further comprising quantitating the level of binding of cells at different locations of the array.

23. The method of claim 21 further comprising characterizing the cells bound at different locations of the array, wherein characterizing comprises counting the cells at different locations, sorting cells at different locations and/or immunostaining the cells at different locations.

24. The method of claim 23 wherein characterizing comprises immunostaining cells at different locations.

25. A method for identifying a modulator of an interaction between a receptor and a ligand, comprising:

(a) contacting cells expressing the receptor or a ligand-binding portion thereof with an immobilized tethered ligand fusion protein in the presence of a test compound and determining the level of binding to the tethered ligand fusion protein;

(b) contacting cells expressing the receptor or a ligand-binding portion thereof with the immobilized tethered ligand fusion protein in the absence of a test compound; and determining the level of binding to the tethered ligand fusion protein; and (c) comparing the level of binding in (a) and (b) for the immobilized tethered ligand fusion protein;

wherein the tethered ligand fusion protein comprises
(i) a ligand domain;
(ii) an intermediate stalk domain; and
(iii) an immobilization domain linked to the stalk domain, and wherein
said ligand domain and said stalk domain are not associated in a naturally occurring protein;

said test compound is other than a known ligand for the receptor; and decreased binding of cells in the presence of the test compound indicates that the test compound is an inhibitor of the interaction between the receptor and the ligand comprising the ligand domain of said tethered ligand fusion protein, and wherein increased binding of cells in the presence of the test compound indicates that the test compound is an enhancer of the interaction between the receptor and the ligand comprising the ligand domain of said tethered ligand fusion protein.

26. The method of claim 25 wherein the stalk domain is carboxy-terminal to the ligand domain, and the immobilization domain is carboxy-terminal to the stalk domain.

27. The method of claim 25 wherein the cell expresses a recombinant receptor.

28. The method of claim 25 wherein the cell expresses a chemokine receptor.

29. The method of claim 27 wherein the cell expresses an orphan receptor.

30. The method of claim 25 wherein
the tethered ligand fusion protein is one of an array of different tethered ligand fusion proteins immobilized to a substrate, different tethered ligand fusion proteins having different ligand domains and immobilized to different locations on the substrate;

steps (a) and (b) comprise contacting the cells with the array of different tethered ligand fusion proteins and determining the level of binding of the cells to the tethered ligand fusion proteins at a plurality of locations of the array.

31. The method of claim 14, wherein characterizing comprises counting the cells at different locations.

32. The method of claim 14, wherein characterizing comprises eluting and sorting the cells at different locations.

33. The method of claim 14, wherein characterizing comprises immunostaining the cells at different locations.

34. The method of claim 16, wherein characterizing comprises counting the cells at different locations.

35. The method of claim 16, wherein characterizing comprises eluting and sorting the cells at different locations.

36. The method of claim 23, wherein characterizing comprises counting the cells at different locations.

37. The method of claim 23, wherein characterizing comprises eluting and sorting the cells at different locations.

* * * * *